United States Patent
Luo et al.

(10) Patent No.: US 10,406,233 B2
(45) Date of Patent: Sep. 10, 2019

(54) TELODENDRIMERS WITH ENHANCED DRUG DELIVERY

(71) Applicant: The Regents of the University of California, Oakland, CA (US)

(72) Inventors: Juntao Luo, Syracuse, NY (US); Kit Lam, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 46 days.

(21) Appl. No.: 14/365,929

(22) PCT Filed: Dec. 19, 2012

(86) PCT No.: PCT/US2012/070508
§ 371 (c)(1),
(2) Date: Jun. 16, 2014

(87) PCT Pub. No.: WO2013/096388
PCT Pub. Date: Jun. 27, 2013

(65) Prior Publication Data
US 2014/0363371 A1   Dec. 11, 2014

Related U.S. Application Data

(60) Provisional application No. 61/578,579, filed on Dec. 21, 2011.

(51) Int. Cl.
| | | |
|---|---|---|
| *A61K 47/32* | (2006.01) | |
| *C08G 83/00* | (2006.01) | |
| *C08L 71/02* | (2006.01) | |
| *C08G 65/333* | (2006.01) | |
| *A61K 47/60* | (2017.01) | |
| *A61K 47/59* | (2017.01) | |
| *A61K 47/64* | (2017.01) | |

(52) U.S. Cl.
CPC ............ *A61K 47/32* (2013.01); *A61K 47/595* (2017.08); *A61K 47/60* (2017.08); *A61K 47/645* (2017.08); *C08G 65/33303* (2013.01); *C08G 65/33396* (2013.01); *C08G 83/004* (2013.01); *C08L 71/02* (2013.01)

(58) Field of Classification Search
None
See application file for complete search history.

(56) References Cited

U.S. PATENT DOCUMENTS

| | | |
|---|---|---|
| 2002/0041898 A1 | 4/2002 | Unger et al. |
| 2003/0027863 A1* | 2/2003 | Cruz ................... A61K 31/222 514/546 |
| 2009/0203706 A1 | 8/2009 | Zhao et al. |
| 2011/0286915 A1 | 11/2011 | Lam et al. |

FOREIGN PATENT DOCUMENTS

| | | |
|---|---|---|
| EP | 1967212 A2 | 9/2008 |
| WO | 2010/039496 A2 | 4/2010 |
| WO | 2012158622 A2 | 11/2012 |

OTHER PUBLICATIONS

Li, et al., "Antimicrobial Activities of Amine- and Guanidine-Functionalized Cholic Acid Derivatives," *Antimicrobial Agents and Chemotherapy*, vol. 43(6), pp. 1347-1349 (1999).
International Search Report and Written Opinion for PCT/US2012/070508 dated Feb. 27, 2013.
Kaminskas et al., "PEGyl at ion of polylysine dendrimers improves absorption and lymphatic targeting following SC administration in rats," Journal of Controlled Release. Elsevier, vol. 140. No. 2, Dec. 3, 2009, pp. 108-116.
Kaminskas et al., "The Impact of Molecular Weight and PEG Chain Length on the Systemic Pharmacokinetics of PEGylated Poly L-Lysine Dendrimers," Molecular Pharmaceutics, vol. 5. No. 3., Jun. 1, 2008, pp. 449-463.
Li et al., "Well-defined, reversible disulfide cross-linked micelles for on-demand paclitaxel delivery," Biomaterials, vol. 32, Issue 27, Sep. 30, 2011, pp. 6633-6645.
Luo et al., "Well-defined, size-tunable, multifunctional micelles for efficient paclitaxel delivery for cancer treatment," Bioconjugate Chem., vol. 21, No. 7, Jul. 2010, pp. 1216-1224.
Xiao et al., "A self-assembling nanoparticle for paclitaxel delivery in ovarian cancer," Biomaterials. vol. 30, Oct. 2009, pp. 6006-6016.
Xiao et al., "PEG-oligocholic acid telodendrimer micelles for the targeted delivery of doxorubicin to B-cell lymphoma," Journal of Controlled release, vol. 155, 2011, pp. 272-281.

* cited by examiner

*Primary Examiner* — James W Rogers
(74) *Attorney, Agent, or Firm* — Mintz, Levin, Cohn, Ferris, Glovsky & Popeo, P. C.

(57) ABSTRACT

The present invention provides amphiphilic telodendrimers that aggregate to form nanocarriers characterized by a hydrophobic core and a hydrophilic exterior. The nanocarrier core may include amphiphilic functionality such as cholic acid or cholic acid derivatives, and the exterior may include branched or linear poly(ethylene glycol) segments. Nanocarrier cargo such as hydrophobic drugs and other materials may be sequester in the core via non-covalent means or may be covalently bound to the telodendrimer building blocks. Telodendrimer structure may be tailored to alter loading properties, interactions with materials such as biological membranes, and other characteristics.

6 Claims, 19 Drawing Sheets

The structure and properties of polymers designed and synthesized for PTX delivery

| | Polymers | Shape | CMC (μg/mL) | Micelle Size (nm) | PTX-Micelle size nm, (PTX: Polymer w/w) |
|---|---|---|---|---|---|
| 1 | PEG$^{2K}$K$_2$CA$_8$ | BT | 8.9 | 24.6 | Multi-peaks (1:4) |
| 2 | PEG$^{2K}$K$_3$CA$_8$ | BT | 12.7 | 19.6 | 28.6 (1:4) |

Blood cell counts on day 7 after the last dosage in the therapeutic study

| Groups | WBC (K/ul) | RBC (M/ul) | Hemoglobin (g/dL) | Platelets (K/uL) |
|---|---|---|---|---|
| PBS | 6.8 ± 1.9 | 7.2 ± 1.0 | 12.9 ± 1.0 | 1032.5 ± 244.1 |
| DOX | 3.3 ± 1.6* | 7.1 ± 0.8 | 11.7 ± 1.4 | 1029.0 ± 363.9 |
| Doxil | 4.6 ± 2.8 | 8.1 ± 0.9 | 12.6 ± 1.3 | 958.2 ± 352.6 |
| DOX-PEG$^{5k}$-CA$_4^a$Rh$_4^\varepsilon$ | 6.1 ± 2.2 | 8.8 ± 0.4 | 13.5 ± 0.8 | 1109.0 ± 261.8 |

TELODENDRIMERS WITH ENHANCED DRUG DELIVERY

CROSS-REFERENCES TO RELATED APPLICATIONS

This application is the U.S. National Stage Entry under § 371 of International Application No. PCT/US2012/070508, filed Dec. 19, 2012, which claims priority to U.S. Provisional Application No. 61/578,579, filed Dec. 21, 2011, which is incorporated in its entirety herein for all purposes.

STATEMENT AS TO RIGHTS TO INVENTIONS MADE UNDER FEDERALLY SPONSORED RESEARCH AND DEVELOPMENT

This invention was made with Government support under Grant Nos. CA 115483 and CA 140449 awarded by the National Institutes of Health. The Government has certain rights in this invention.

BACKGROUND OF THE INVENTION

Several effective chemotherapeutic agents for treatment of various cancer types are very insoluble in water, requiring formulations that induce unwanted side effects. Recently, nanotherapeutic formulations such as Abraxane® (paclitaxel-loaded albumin nanoparticles), Doxil® (doxorubicin-loaded liposomes), and others have been shown to improve the clinical toxicity profiles of the drugs, but their anti-tumor effects are only marginally better than the original drug formulations. This has been attributed in part to the relatively large size of the nanotherapeutic formulations (generally >100 nm), which limits the extent to which the drugs can penetrate into tumor mass. In some cases, this large size also causes nanotherapeutics to be trapped in the liver and reticuloendothelial system (RES). Accordingly, there is a need to develop smaller (20-80 nm) stealth and biocompatible nanocarriers for effective delivery anti-cancer drugs in vivo.

We have recently developed several novel nanocarriers for paclitaxel (PTX) or other hydrophobic drugs. These novel nanocarriers, comprising poly(ethylene glycol) (PEG) and oligo-cholic acids, can self-assemble under aqueous conditions to form core-shell (cholane-PEG) structures that can carry PTX in the hydrophobic interior. These amphiphilic drug-loaded nanoparticles are therapeutic by themselves with improved clinical toxicity profiles. More importantly, when decorated with cancer cell surface targeting ligands and/or tumor blood vessel ligands, these nanocarriers will be able to deliver toxic therapeutic agents to the tumor sites. The final size of the nanocarriers (10 to 100 nm) is tunable by using various, or a combination of, different cholane-PEG preparations. The nanocarrier components, PEG and cholic acid, are all biocompatible and largely non-toxic. Indeed, the PTX nanotherapeutics exhibited safe profile in in vivo administration for anticancer treatment in mouse models and companion dogs. However, the nanocarriers have demonstrated some hemolytic activity both in vitro and in vivo, as well as reduced loading capacity for certain drugs. Therefore, there is a need to develop nanocarriers with improved biocompatibility and versatility.

The present invention is based on the surprising discovery that certain changes to the hydrophilic and hydrophobic segments of the constituent building blocks improve the therapeutic properties without disrupting nanocarrier assembly, addressing the needs described above.

BRIEF SUMMARY OF THE INVENTION

In a first aspect, the present invention provides a compound of formula I:

$$(PEG)_m\text{-}A\text{-}L\text{-}D\text{-}(R)_n \quad (I)$$

wherein radical D of formula I is a dendritic polymer having a single focal point group, a plurality of branched monomer units X and a plurality of end groups. Radical L of formula I is a bond or a linker linked to the focal point group of the dendritic polymer. Each PEG in formula I is a polyethyleneglycol (PEG) polymer, wherein each PEG polymer has a molecular weight of 1-100 kDa. Radical A of formula I is a monomer or oligomer linked to at least two PEG groups. Each R of formula I is independently the end group of the dendritic polymer, a hydrophobic group, a hydrophilic group, an amphiphilic compound or a drug, such that when R is not an end group each R is linked to one of the end groups. Subscript n of formula I is an integer from 2 to 20, wherein subscript n is equal to the number of end groups on the dendritic polymer, and wherein at least half the number n of R groups are each independently a hydrophobic group, a hydrophilic group, an amphiphilic compound or a drug. Subscript m of formula I is an integer from 2 to 20.

In a second aspect, the invention provides a nanocarrier having an interior and an exterior, the nanocarrier including a plurality of compounds of formula I, wherein each compound self-assembles in an aqueous solvent to form the nanocarrier such that a hydrophobic pocket is formed in the interior of the nanocarrier, and wherein the PEG of each compound self-assembles on the exterior of the nanocarrier.

In as third aspect, the invention provides a method of treating a disease, including administering to a subject in need of such treatment, a therapeutically effective amount of a nanocarrier as described above, wherein the nanocarrier further comprises a drug.

In a fourth aspect, the invention provides a method of imaging, including administering to a subject to be imaged, an effective amount of a nanocarrier as described above, wherein the nanocarrier further comprises an imaging agent.

In a fifth aspect, the invention provides a compound of formula II:

$$(PEG)_m\text{-}L\text{-}D\text{-}(R)_n \quad (II)$$

wherein radical D of formula II is a dendritic polymer having a single focal point group, a plurality of branched monomer units X and a plurality of end groups. Radical L of formula II is a bond or a linker linked to the focal point group of the dendritic polymer. Each PEG of formula II is a polyethyleneglycol (PEG) polymer, wherein each PEG polymer has a molecular weight of 1-100 kDa. Each R of formula II is independently a hydrophobic group, a hydrophilic group, an amphiphilic compound or a drug, wherein at least two different R groups are present. Subscript n of formula II is an integer from 2 to 20, wherein subscript n is equal to the number of end groups on the dendritic polymer, and wherein at least half the number n of R groups are each independently a hydrophobic group, a hydrophilic group, an amphiphilic compound or a drug. Subscript m of formula II is 0 or 1.

BRIEF DESCRIPTION OF THE DRAWINGS

FIG. 16 summarizes the blood cell counts on day 7 after the last dosage in the therapeutic study.

DETAILED DESCRIPTION OF THE INVENTION

I. General

Figure 1:
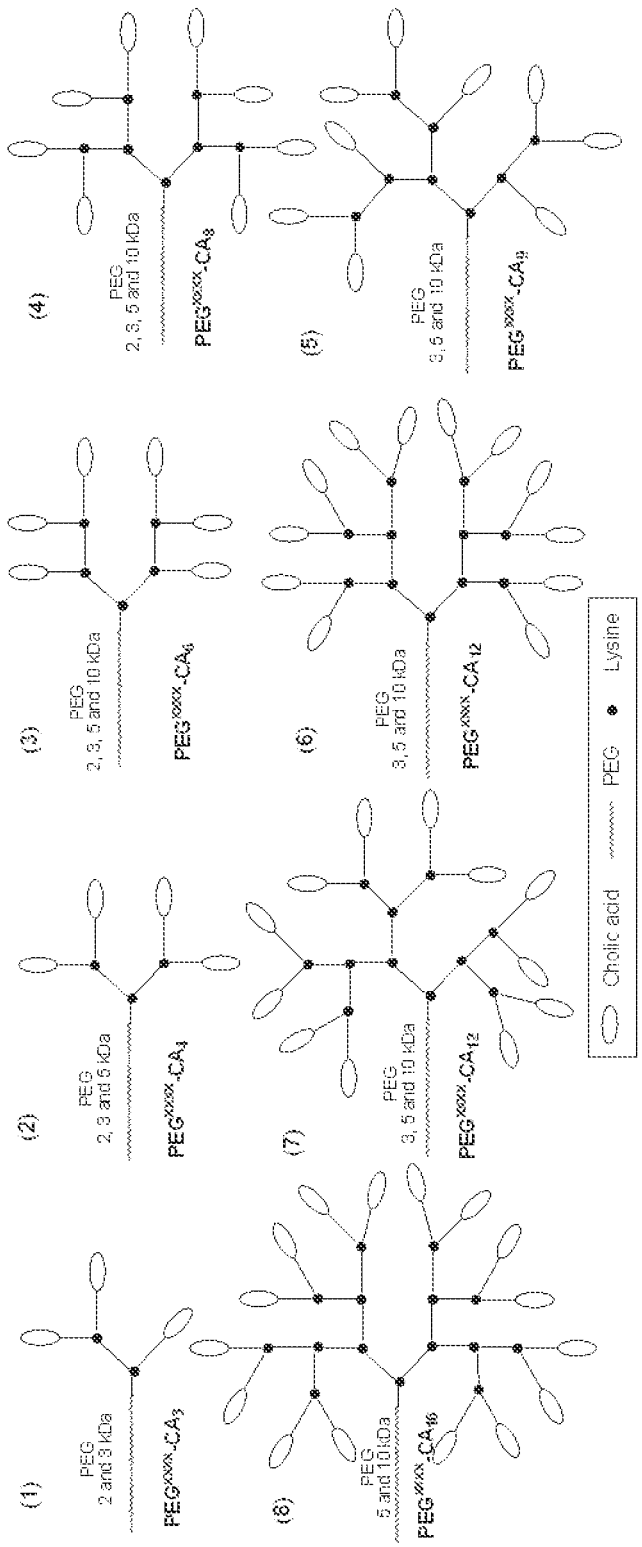
FIG. 1 shows examples of telodendrimer architectures.

The present invention provides telodendrimers having a hydrophilic poly(ethylene glycol) (PEG) segment as well as a branched hydrophobic segment or a branched amphiphilic segment. The PEG segment of the telodendrimers can contain one or more PEG chains with linear or branched architectures. Hybrid telodendrimers are also described and possess covalently bound cargo moieties such as cholic acid groups and hydrophobic drugs. The telodendrimers can aggregate to form nanocarriers having a hydrophobic interior and a hydrophilic exterior. The hydrophobic core of the nanocarriers can be provided by cholic acid, which has a hydrophobic face and a hydrophilic face. The cholic acid moieties can be chemically modified to alter nanocarrier assembly and stability. For example, cholic acid derivatives with modified hydrophilic faces can be used. The nanocarriers can non-covalently sequester hydrophobic drugs or other cargo having low water solubility for delivery to a subject.

II. Definitions

As used herein, the terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendrimer can be attached to other segments of the compounds of the invention, and the end groups may be further functionalized with additional chemical moieties.

As used herein, the term "telodendrimer" refers to a dendrimer containing a hydrophilic PEG segment and one or more chemical moieties covalently bonded to one or more end groups of the dendrimer. These moieties can include, but are not limited to, hydrophobic groups, hydrophilic groups, amphiphilic compounds, and drugs. Different moieties may be selectively installed at a desired end groups using orthogonal protecting group strategies.

As used herein, the term "bow-tie dendrimer" or "bow-tie telodendrimer" refers to a dendrimer containing two branched segments, such as a dendrimer and a branched PEG moiety, that are linked together at their focal points using a linker moiety.

As used herein, the terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendritic polymer can be attached to other segments of the telodendrimers, and the end groups may be further functionalized with additional chemical moieties.

As used herein, the term "nanocarrier" refers to a micelle resulting from aggregation of the dendrimer conjugates of the invention. The nanocarrier has a hydrophobic core and a hydrophilic exterior.

As used herein, the terms "monomer" and "monomer unit" refer to a diamino carboxylic acid, a dihydroxy carboxylic acid and a hydroxyl amino carboxylic acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl)pentanoic acid. Examples of dihydroxy carboxylic acid groups of the present invention include, but are not limited to, glyceric acid, 2,4-dihydroxybutyric acid, glyceric acid, 2,4-dihydroxybutyric acid, 2,2-Bis(hydroxymethyl)propionic acid and 2,2-Bis(hydroxymethyl) butyric acid. Examples of hydroxyl amino carboxylic acids include, but are not limited to, serine and homoserine. One of skill in the art will appreciate that other monomer units are useful in the present invention.

As used herein, the term "amino acid" refers to a carboxylic acid bearing an amine functional group. Amino acids include the diamino carboxylic acids described above. Amino acids include naturally occurring α-amino acids, wherein the amine is bound to the carbon adjacent to the carbonyl carbon of the carboxylic acid. Examples of naturally occurring α-amino acids include, but are not limited to, L-aspartic acid, L-glutamic acid, L-histidine, L-lysine, and L-arginine. Amino acids may also include the D-enantiomers of naturally occurring α-amino acids, as well as β-amino acids and other non-naturally occurring amino acids.

As used herein, the term "linker" refers to a chemical moiety that links one segment of a dendrimer conjugate to another. The types of bonds used to link the linker to the segments of the dendrimers include, but are not limited to, amides, amines, esters, carbamates, ureas, thioethers, thiocarbamates, thiocarbonate and thioureas. One of skill in the art will appreciate that other types of bonds are useful in the present invention.

As used herein, the term "oligomer" refers to five or fewer monomers, as described above, covalently linked together. The monomers may be linked together in a linear or branched fashion. The oligomer may function as a focal point for a branched segment of a telodendrimer.

As used herein, the term "hydrophobic group" refers to a chemical moiety that is water-insoluble or repelled by water. Examples of hydrophobic groups include, but are not limited to, long-chain alkanes and fatty acids, fluorocarbons, silicones, certain steroids such as cholesterol, and many polymers including, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as PEG.

As used herein, the term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic compounds useful in the present invention include, but are not limited to, cholic acid and cholic acid analogs and derivatives.

As used herein, the term "cholic acid" refers to (R)-4-((3R,5S,7R,8R,9S,10S,12S, 13R,14S,17R)-3,7,12-trihydroxy-10,13-dimethylhexadecahydro-1H-cyclopenta[a] phenanthren-17-yl)pentanoic acid. Cholic acid is also know as 3α,7α,12α-trihydroxy-5β-cholanoic acid; 3-α,7-α,12-α-Trihydroxy-5-β-cholan-24-oic acid; 17-β-(1-methyl-3-carboxypropyl)etiocholane-3α,7α,12α-triol; cholalic acid; and cholalin. Cholic acid derivatives and analogs, such as allocholic acid, pythocholic acid, avicholic acid, deoxycholic acid, chenodeoxycholic acid, are also useful in the present invention. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

As used herein, the terms "drug" or "therapeutic agent" refers to an agent capable of treating and/or ameliorating a condition or disease. A drug may be a hydrophobic drug, which is any drug that repels water. Hydrophobic drugs useful in the present invention include, but are not limited to, paclitaxel, doxorubicin, etoposide, irinotecan, SN-38, cyclosporin A, podophyllotoxin, Carmustine, Amphotericin, Ixabepilone, Patupilone (epothelone class), rapamycin and platinum drugs. The drugs of the present invention also include prodrug forms. One of skill in the art will appreciate that other drugs are useful in the present invention.

As used herein, the term "imaging agent" refers to chemicals that allow body organs, tissue or systems to be imaged. Exemplary imaging agents include paramagnetic agents, optical probes, and radionuclides.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g. Lieberman, *Pharmaceutical Dosage Forms* (vols. 1-3, 1992): Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott. Williams & Wilkins). In sensitized cells, the therapeutically effective dose can often be lower than the conventional therapeutically effective dose for non-sensitized cells.

III. Telodendrimers

The invention provides amphiphilic telodendrimer conjugates having a hydrophilic poly(ethylene glycol) (PEG) segment and a hydrophobic segment. The PEG segment can have a branched or linear architecture including one or more PEG chains. Bow-tie telodendrimers contain a branched PEG segment containing at least two PEG chains. The hydrophobic segment of the telodendrimer can be provided by cholic acid, which has a hydrophobic face and a hydrophilic face. The cholic acid and the PEG are connected by oligomers and/or polymers that can contain a variety of acid repeats units. Typically, the oligomers and polymers comprise a diamino carboxylic acid, lysine. The telodendrimers can aggregate in solution to form micelles with a hydrophobic interior and a hydrophilic exterior. The micelles can be used as nanocarriers to deliver drugs or other agents having low water solubility.

The present invention provides a PEGylated dendrimer, referred to as a telodendrimer, containing cholic acid groups and other moieties at the dendrimer periphery. In some embodiments, the invention provide a compound of formula II:

$(PEG)_m\text{-L-D-}(R)_n$            (II)

wherein radical D of formula II is a dendritic polymer having a single focal point group, a plurality of branched monomer units X and a plurality of end groups. Radical L of formula II is a bond or a linker linked to the focal point group of the dendritic polymer. Each PEG of formula II is a polyethyleneglycol (PEG) polymer, wherein each PEG polymer has a molecular weight of 1-100 kDa. Each R of formula II is independently the end group of the dendritic polymer, a hydrophobic group, a hydrophilic group, an amphiphilic compound or a drug, such that when R is not an end group each R is linked to one of the end groups. Subscript n of formula II is an integer from 2 to 20, wherein subscript n is equal to the number of end groups on the dendritic polymer, and wherein at least half the number n of R groups are each independently a hydrophobic group, a hydrophilic group, an amphiphilic compound or a drug. Subscript m of formula II is 0 or 1.

In some embodiments, at least two different R groups are present, such as two different amphiphilic groups, or an amphilic group and a drug, or an amphiphilic group and a dendritic polymer end group, or two different drugs, or a drug and a dendritic end group.

The dendritic polymer can be any suitable dendritic polymer. The dendritic polymer can be made of branched monomer units including amino acids or other bifunctional AB2-type monomers, where A and B are two different functional groups capable of reacting together such that the resulting polymer chain has a branch point where an A-B bond is formed. In some embodiments, each branched monomer unit X can be a diamino carboxylic acid, a dihydroxy carboxylic acid and a hydroxyl amino carboxylic acid. In some embodiments, each diamino carboxylic acid can be 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid or 5-amino-2-(3-aminopropyl)pentanoic acid. In some embodiments, each dihydroxy carboxylic acid can be glyceric acid, 2,4-dihydroxybutyric acid, 2,2-Bis(hydroxymethyl)propionic acid, 2,2-Bis(hydroxymethyl)butyric acid, serine or threonine. In some embodiments, each hydroxyl amino carboxylic acid can be serine or homoserine. In some embodiments, the diamino carboxylic acid is an amino acid. In some embodiments, each branched monomer unit X is lysine.

Figure 2:
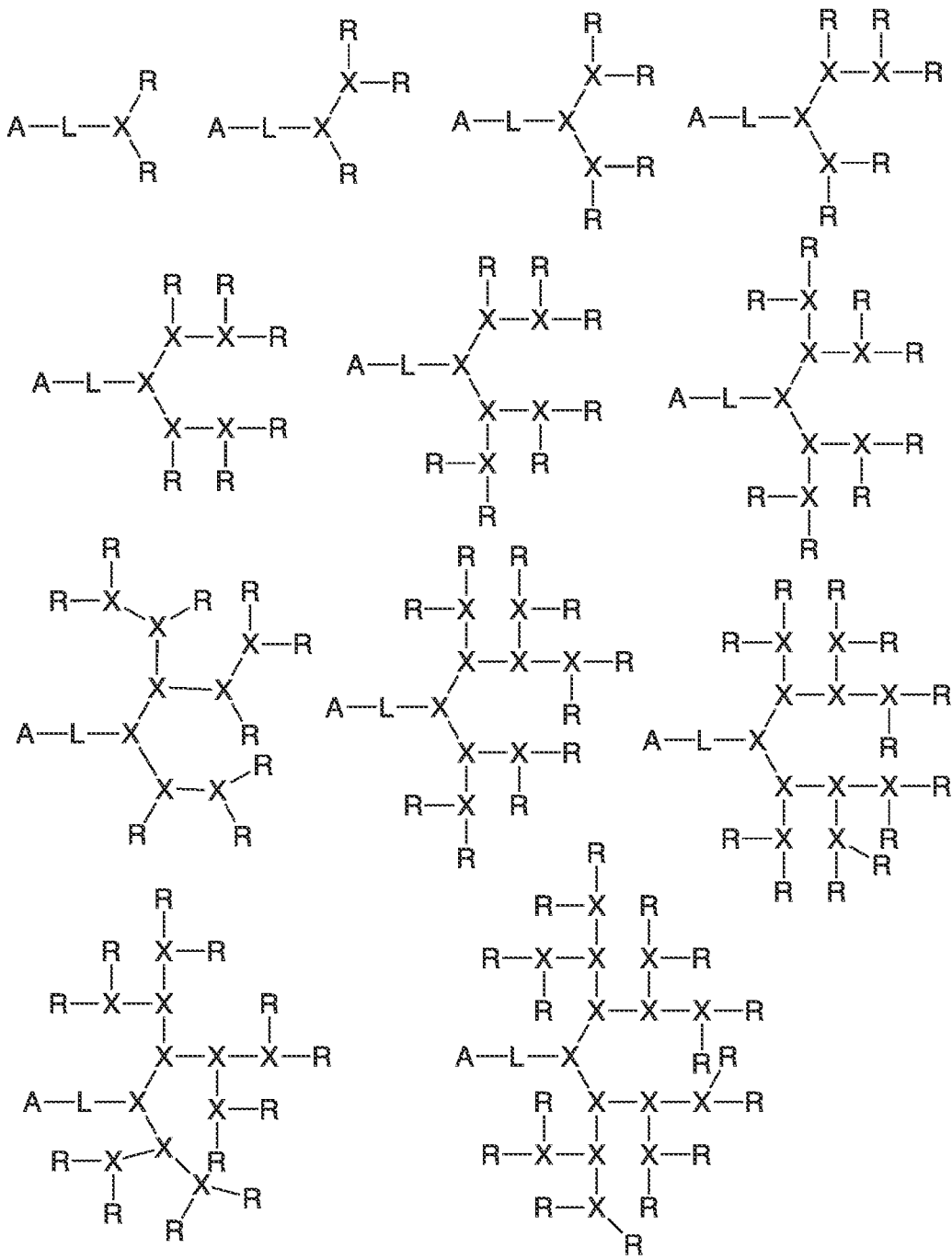
FIG. 2 shows various architectures of the A-L-D-(R)$_n$ segment of the bow-tie telodendrimers.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. See, for example, the structures in FIG. 2. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

The focal point of a telodendrimer or a telodendrimer segment may be any suitable functional group. In some embodiments, the focal point includes a functional group that allows for attachment of the telodendrimer or telodendrimer segment to another segment. The focal point functional group can be a nucleophilic group including, but not limited to, an alcohol, an amine, a thiol, or a hydrazine. The focal point functional group may also be an electrophile such as an aldehyde, a carboxylic acid, or a carboxylic acid derivative including an acid chloride or an N-hydroxysuccinimidyl ester.

The R groups installed at the telodendrimer periphery can be any suitable chemical moiety, including hydrophilic groups, hydrophobic groups, or amphiphilic compounds. Examples of hydrophobic groups include, but are not limited to, long-chain alkanes and fatty acids, fluorocarbons, silicones, certain steroids such as cholesterol, and many polymers including, for example, polystyrene and polyisoprene. Examples of hydrophilic groups include, but are not limited to, alcohols, short-chain carboxylic acids, amines, sulfonates, phosphates, sugars, and certain polymers such as PEG. Examples of amphiphilic compounds include, but are not limited to, molecules that have one hydrophilic face and one hydrophobic face.

Amphiphilic compounds useful in the present invention include, but are not limited to, cholic acid and cholic acid analogs and derivatives. "Cholic acid" refers to (R)-4-((3R, 5S, 7R,8R,9S,10S,12S,13R,14S,17R)-3,7,12-trihydroxy-10, 13-dimethylhexadecahydro-1H-cyclopenta[a]phenanthren-17-yl)pentanoic acid, having the structure:

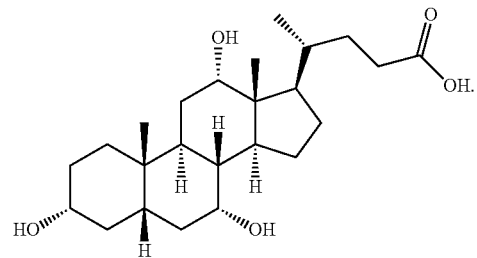

Cholic acid derivatives and analogs include, but are not limited to, allocholic acid, pythocholic acid, avicholic acid, deoxycholic acid, and chenodeoxycholic acid. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

Telodendrimer end groups may also include drugs such as paclitaxel, doxorubicin, etoposide, irinotecan, SN-38, cyclosporin A, podophyllotoxin, carmustine, amphotericin, ixabepilone, patupilone (epothelone class), rapamycin and platinum drugs. One of skill in the art will appreciate that other drugs are useful in the present invention.

In some embodiments, each R can be cholic acid, (3α,5β,7α,12α)-7,12-dihydroxy-3-(2,3-dihydroxy-1-propoxy)-cholic acid, (3α,5β,7α,12α)-7-hydroxy-3,12-di(2,3-dihydroxy-1-propoxy)-cholic acid, (3α,5β,7α,12α)-7,12-dihydroxy-3-(3-amino-2-hydroxy-1-propoxy)-cholic acid, cholesterol formate, doxorubicin, or rhein.

The telodendrimer backbone can vary, depending on the number of branches and the number and chemical nature of the end groups and R groups, which will modulate solution conformation, rheological properties, and other characteristics. The telodendrimers can have any suitable number n of end groups and any suitable number of R groups. In some embodiments, n can be 2-70, or 2-50, or 2-30, or 2-10. In some embodiment, n is 2-20.

The telodendrimer can have a single type of R group on the periphery, or any combination of R groups in any suitable ratio. In general, at least half the number n of R groups are other than an end group. For example, at least half the number n of R groups can be a hydrophobic group, a hydrophilic group, an amphiphilic compound, a drug, or any combination thereof. In some embodiments, half the number n of R groups are amphiphilic compounds. Examples of telodendrimers include, but are not limited to, those found depicted in FIG. 1.

In some embodiments, the compound can have either of the formulas:

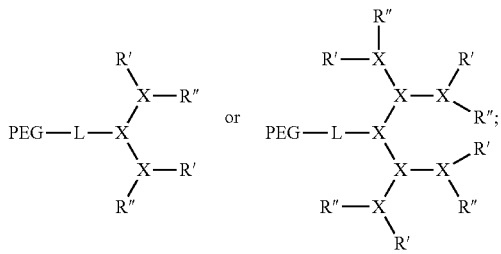

wherein each branched monomer unit X is lysine; and R' and R" are each independently the end group of the dendritic polymer, a hydrophobic group, a hydrophilic group, an amphiphilic compound or a drug, such that R' and R" are different. In some embodiments, each R' can be cholic acid (CA), (3α,5β,7α,12α)-7,12-dihydroxy-3-(2,3-dihydroxy-1-propoxy)-cholic acid (CA-4OH), (3α,5β,7α,12α)-7-hydroxy-3,12-di(2,3-dihydroxy-1-propoxy)-cholic acid (CA-5OH) or (3α,5β,7α,12α)-7,12-dihydroxy-3-(3-amino-2-hydroxy-1-propoxy)-cholic acid (CA-3OH—NH$_2$); and each R" can be cholesterol formate (CF), doxorubicin (DOX), and rhein (Rh).

In some embodiments, the compound has the formula:

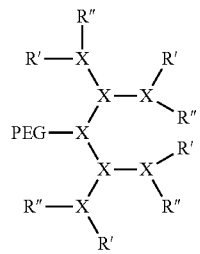

wherein each X is lysine; PEG is PEG5k; and each R' and R" is CA-4OH, or each R' and R" is CA-5OH, or each R' and R" is CA-3OH—NH$_2$.

In some embodiments, the compound has the formula:

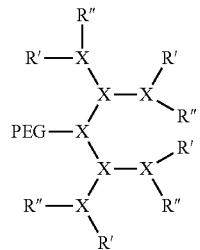

wherein each X is lysine. Each R' is linked to the lysine a amine and each R" is linked to the lysine ε amine. PEG is PEG5k. Each R' is CA, and each R" is CF; or each R' is CF, and each R" is CA; or each R' and R" is Rh; or each R' is CA, and each R" is Rh; or each R' is Rh, and each R" is CA.

In some embodiments, the compound has the formula:

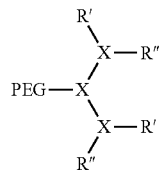

wherein each X is lysine; PEG is PEG(10k); and each R' and R" is DOX.

The linker L can include any suitable linker. In general, the linkers are bifunctional linkers, having two functional groups for reaction with each of two telodendrimer segments. In some embodiments, the linker can be a heterobifunctional linker. In some embodiments, the linker can be a homobifunctional linker. In some embodiments, the linker L can be polyethylene glycol, polyserine, polyglycine, poly (serine-glycine), aliphatic amino acids, 6-amino hexanoic acid, 5-amino pentanoic acid, 4-amino butanoic acid or beta-alanine. One of skill in the art will recognize that the size and chemical nature of the linker can be varied based on the structures of the telodendrimer segments to be linked.

In some embodiments, linker L has the formula:

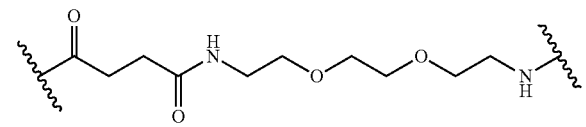 [SMILES: *NCCOCCOCCNC(=O)CCC(*)=O]

Polyethylene glycol (PEG) polymers of any size and architecture are useful in the nanocarriers of the present invention. In some embodiments, the PEG is from 1-100 kDa. In other embodiments, the PEG is from 1-10 kDa. In some other embodiments, the PEG is about 3 kDa. In still other embodiments, additional PEG polymers are linked to the amphiphilic compounds. For example, when the amphiphilic compound is cholic acid, up to 3 PEG polymers are linked to each cholic acid. The PEG polymers linked to the amphiphilic compounds are from 200-10,000 Da in size. In yet other embodiments, the PEG polymers linked to the amphiphilic compounds are from 1-5 kDa in size. One of skill in the art will appreciate that other PEG polymers and other hydrophilic polymers are useful in the present invention. PEG can be any suitable length.

IV. Telodendrimers with Branched PEG Moieties

The bow-tie telodendrimers of the present invention contain two branched segments that are linked together at their focal points. Generally, the bow-tie telodendrimers include any telodendrimer as described above or as described previously (WO 2010/039496) and branched PEG segment containing two or more PEG chains bound to an oligomer focal point. Some embodiments of the present invention provide a compound of formula I:

$$(PEG)_m\text{-}L\text{-}D\text{-}(R)_n \qquad (II)$$

wherein D, L, and PEG are described as above. Radical A of formula I is a monomer or oligomer linked to at least two PEG groups. Each R of formula I is independently the end group of the dendritic polymer, a hydrophobic group, a hydrophilic group, an amphiphilic compound or a drug, such that when R is not an end group each R is linked to one of the end groups. Subscript n of formula I is an integer from 2 to 20, wherein subscript n is equal to the number of end groups on the dendritic polymer, and wherein at least half the number n of R groups are each independently a hydrophobic group, a hydrophilic group, an amphiphilic compound or a drug. Subscript m of formula I is an integer from 2 to 20.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. See, for example, the structures in FIG. 2. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

In some embodiments, the compound can be:

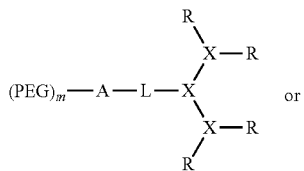

or

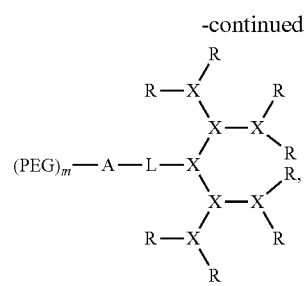

wherein each branched monomer unit X is lysine.

In some embodiments, the compound can be:

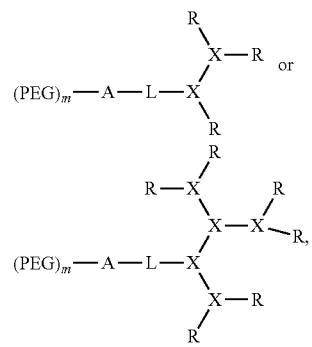

wherein each branched monomer unit X is lysine.

The PEG-oligomer unit in the bow-tie telodendrimers may contain any suitable number of PEG moieties. PEG moieties may be installed site-selectively at various positions on the oligomer using orthogonal protecting groups. In some embodiments, the $(PEG)_m$-A portion of the compound can be:

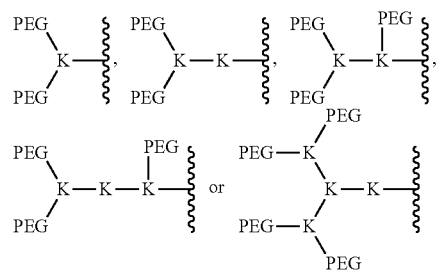

wherein each K is lysine.

In some embodiments, the telodendrimer can be:

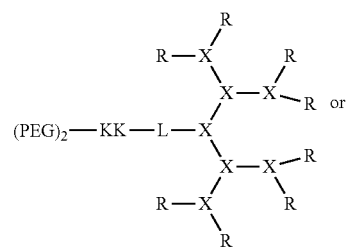

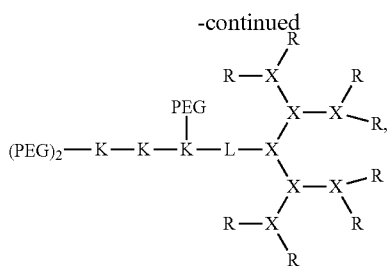

wherein each K is lysine; each PEG is PEG2k; each branched monomer unit X is lysine; each R is cholic acid; and linker L has the formula:

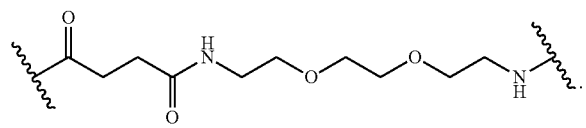

V. Nanocarriers

The telodendrimers of the present invention aggregate to form nanocarriers with a hydrophobic core and a hydrophilic exterior. In some embodiments, the invention provides a nanocarrier having an interior and an exterior, the nanocarrier comprising a plurality of the dendrimer conjugates of the invention, wherein each compound self-assembles in an aqueous solvent to form the nanocarrier such that a hydrophobic pocket is formed in the interior of the nanocarrier, and wherein the PEG of each compound self-assembles on the exterior of the nanocarrier.

In some embodiments, the nanocarrier includes a hydrophobic drug or an imaging agent, such that the hydrophobic drug or imaging agent is sequestered in the hydrophobic pocket of the nanocarrier. Hydrophobic drugs useful in the nanocarrier of the present invention includes any drug having low water solubility. In some embodiments, the hydrophobic drug in the nanocarrier can be bortezomib, paclitaxel, SN38, camptothecin, etoposide and doxorubicin, docetaxel, daunorubicin, VP16, prednisone, dexamethasone, vincristine, vinblastine, temsirolimus and carmusine.

In some embodiments, the nanocarrier includes at least one monomer unit that is optionally linked to an optical probe, a radionuclide, a paramagnetic agent, a metal chelate or a drug. The drug can be a variety of hydrophilic or hydrophobic drugs, and is not limited to the hydrophobic drugs that are sequestered in the interior of the nanocarriers of the present invention.

Drugs that can be sequestered in the nanocarriers or linked to the conjugates of the present invention include, but are not limited to, cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present invention include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the present invention.

Other drugs useful in the present invention also include radionuclides, such as $^{67}Cu$, $^{90}Y$, $^{123}I$, $^{125}I$, $^{131}I$, $^{177}Lu$, $^{188}Re$, $^{186}Re$ and $^{211}At$. In some embodiments, a radionuclide can act therapeutically as a drug and as an imaging agent.

Imaging agents include paramagnetic agents, optical probes and radionuclides. Paramagnetic agents include iron particles, such as iron nanoparticles that are sequestered in the hydrophobic pocket of the nanocarrier.

Some embodiments of the invention provide nanocarriers wherein each amphiphilic compound R is independently cholic acid, allocholic acid, pythocholic acid, avicholic acid, deoxycholic acid, or chenodeoxycholic acid.

VI. Method of Treating

The nanocarriers of the present invention can be used to treat any disease requiring the administration of a drug, such as by sequestering a hydrophobic drug in the interior of the nanocarrier, or by covalent attachment of a drug to a conjugate of the nanocarrier. The nanocarriers can also be used for imaging, by sequestering an imaging agent in the interior of the nanocarrier, or by attaching the imaging agent to a conjugate of the nanocarrier.

In some embodiments, the present invention provides a method of treating a disease, including administering to a subject in need of such treatment, a therapeutically effective amount of a nanocarrier of the present invention, wherein the nanocarrier includes a drug. The drug can be a covalently attached to a conjugate of the nanocarrier. In some embodiments, the drug is a hydrophobic drug sequestered in the interior of the nanocarrier. In some embodiments, the nanocarrier also includes an imaging agent. The imaging agent can be a covalently attached to a conjugate of the nanocarrier, or the imaging agent can be sequestered in the interior of the nanocarrier. In some other embodiments, both a hydrophobic drug and an imaging agent are sequestered in the interior of the nanocarrier. In still other embodiments, both a drug and an imaging agent are covalently linked to a conjugate or conjugates of the nanocarrier. In yet other embodiments, the nanocarrier can also include a radionuclide.

The nanocarriers of the present invention can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

Other diseases that can be treated by the nanocarriers of the present invention include: (I) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis: psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome).

In addition, the nanocarriers of the present invention are useful for the treatment of infection by pathogens such as viruses, bacteria, fungi, and parasites. Other diseases can be treated using the nanocarriers of the present invention.

A. Formulations

The nanocarriers of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Pharmaceutical preparations useful in the present invention also include extended-release formulations. In some embodiments, extended-release formulations useful in the present invention are described in U.S. Pat. No. 6,699,508, which can be prepared according to U.S. Pat. No. 7,125,567, both patents incorporated herein by reference.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present invention, the pharmaceutical compositions can be used alone, or in combination with other therapeutic or diagnostic agents.

B. Administration

The nanocarriers of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

VII. Method of Imaging

In some embodiments, the present invention provides a method of imaging, including administering to a subject to be imaged, an effective amount of a nanocarrier of the present invention, wherein the nanocarrier includes an imaging agent. In other embodiments, the method of treating and the method of imaging are accomplished simultaneously using a nanocarrier having both a drug and an imaging agent.

Exemplary imaging agents include paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present invention include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present invention include, but are not limited to, $^3$H, $^{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am.

VIII. Examples

Example 1. Synthesis of Bow-Tie Polymer PEG$^{2k}_2$CA$_8$

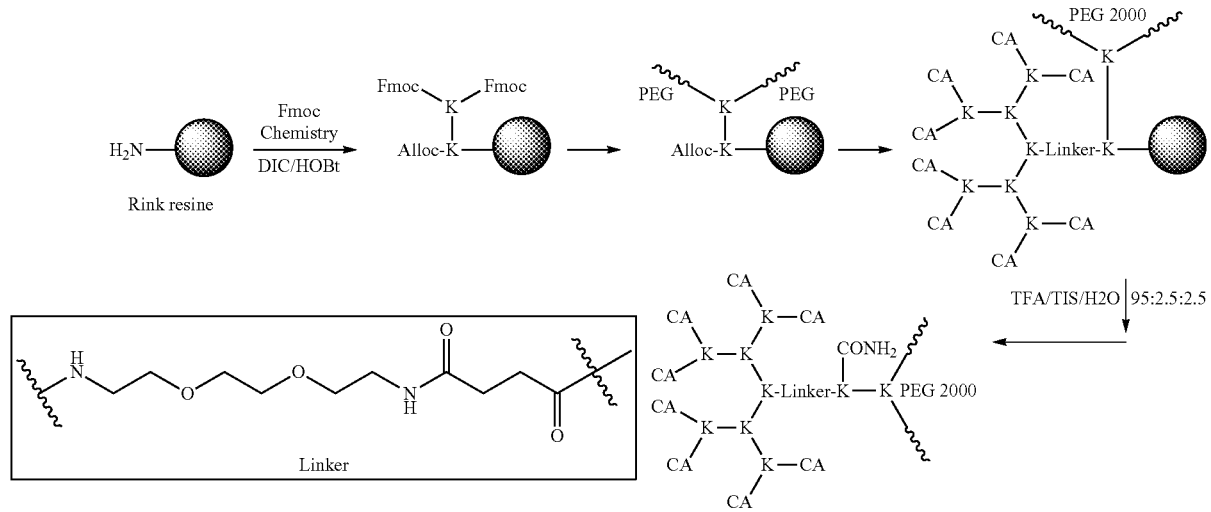

The bow-tie shaped polymer was synthesized on solid resin via Fmoc peptide chemistry. Fmoc protection group on Rink Amide resin was removed via a treatment of 20% 4-methyl piperidine in DMF. (Alloc)-Lys(Fmoc)-OH was conjugated onto free amino group on resin using HOBt/DIC as coupling reagents. After remove Fmoc group on resin, a (Fmoc)$_2$Lys-OH was coupled onto resin. Then PEG-COOH (2000 Da) was conjugated to two amino groups on resin via HOBt/DIC conjugation after remove of Fmoc groups. Then Alloc protection group was removed via the treatment of (P(Ph)3)4Pd in DCM. Then a FmocNH-EG-OH linker was conjugated onto resin, then a branched polylysine was synthesized on bead consequently using Fmoc2Lys-OH as building block. At the end, the free amino groups of the third generation of dendritic polylysine were capped with cholic acid OSu ester. Then, the resin was treated with a TFA/TIS/water (95:2.5:2.5) mixture solution to cleave the bow-tie polymer into solution. The cleavage solution was removed via air blowing then the polymer was precipitated by ice-chilled ether and washed three times with chilled ether.

Example 2. Synthesis of Bow-Tie Polymer PEG$^{2k}_3$CA$_8$

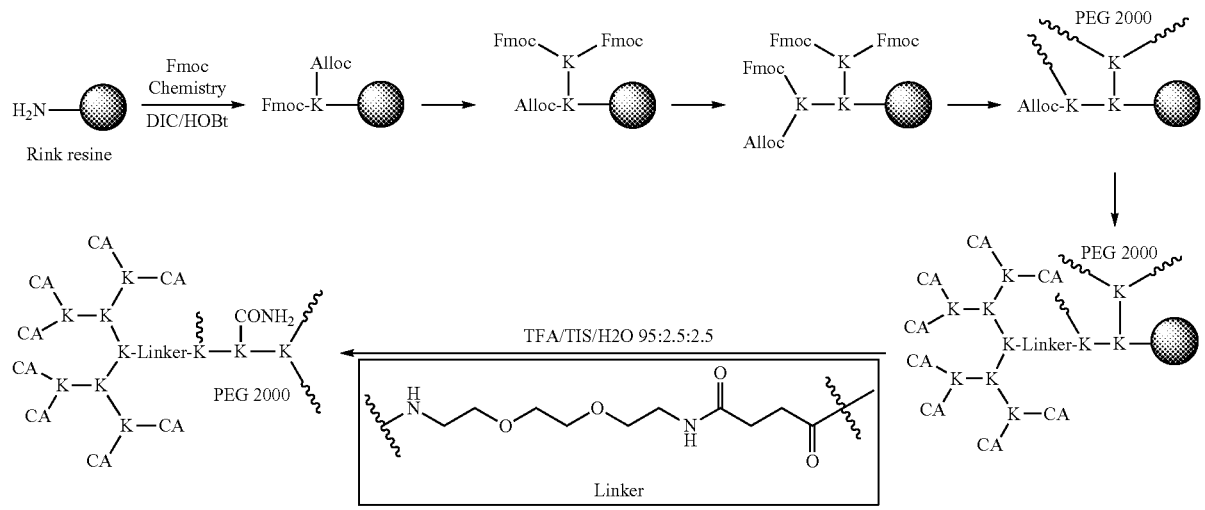

The bow-tie shaped polymer was synthesized on solid resin via Fmoc peptide chemistry. Fmoc protection group on Rink Amide resin was removed via a treatment of 20% 4-methyl piperidine in DMF. (Alloc)-Lys(Fmoc)-OH was conjugated onto free amino group on resin using HOBt/DIC as coupling reagents. After remove Fmoc group on resin, a (Fmoc)$_2$Lys-OH was coupled onto resin. The Alloc protection group was removed via the treatment of (P(Ph)3)4Pd in DCM, and another (Alloc)-Lys(Fmoc)-OH was conjugated onto free amino group on resin using HOBt/DIC as coupling reagents. Then PEG-COOH (2000 Da) was conjugated to three amino groups on resin via HOBt/DIC conjugation after removal of Fmoc groups. Then Alloc protection group was removed via the treatment of (P(Ph)3)4Pd in DCM. Then a FmocNH-EG-OH linker was conjugated onto resin, then a branched polylysine was synthesized on bead consequently using Fmoc2Lys-OH as building block. At the end, the free amino groups of the third generation of dendritic polylysine were capped with cholic acid OSu ester. Then, the resin was treated with a TFA/TIS/water (95:2.5:2.5) mixture solution to cleave the bow-tie polymer into solution. The cleavage solution was removed via air blowing then the polymer was precipitated by ice-chilled ether and washed three times with chilled ether.

Example 3. Characterization of Bow-Tie Polymers

Figure 3:
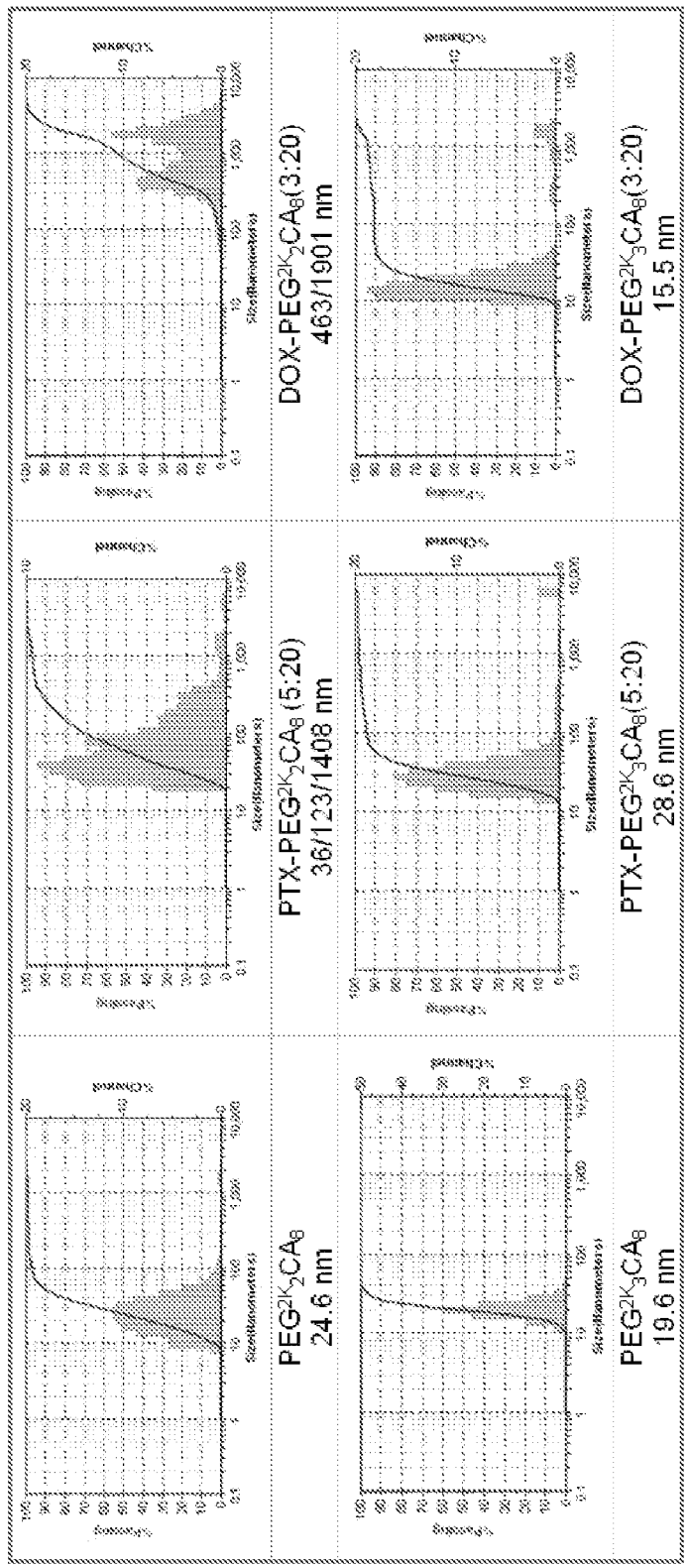
FIG. 3 shows particle sizes and drug loading capacity of the bow-tie shaped polymers 1 and 2 before and after loading with PTX and DOX.
Figure 4:
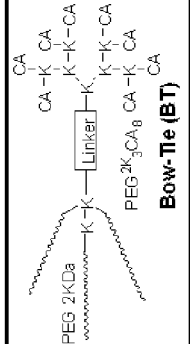
FIG. 4 shows the structure and properties of polymers designed and synthesized for PTX delivery.
Figure 5:
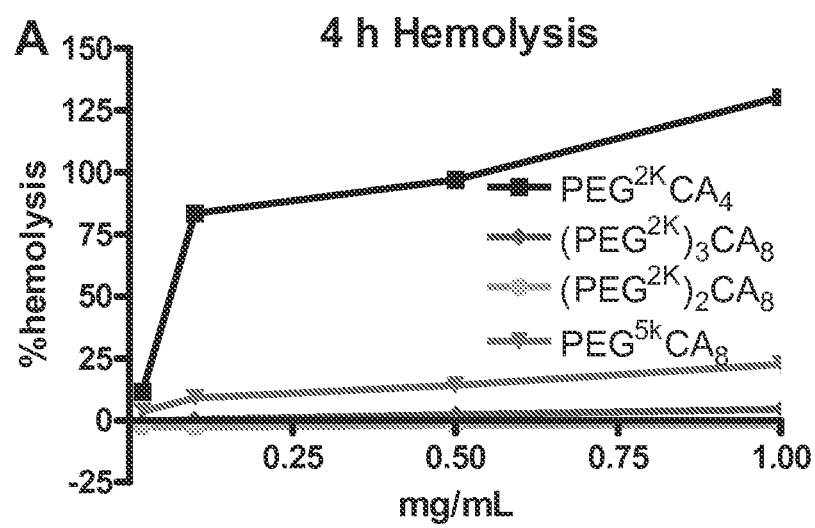
FIG. 5 shows the hemolytic properties of the Bow-tie polymers (PEG$^{2k}$)2CA$_8$ and (PEG$^{2k}$)3CA$_8$ in comparison with PEG$^{5k}$CA$_8$ and PEG$^{2k}$CA$_4$ at different time points: (A) 4 h and (B) 20 h. Bow-tie shaped polymers exhibited minimum hemolytic properties even at the highest concentration of 1 mg/mL after incubation for 20 h.
Figure 5:
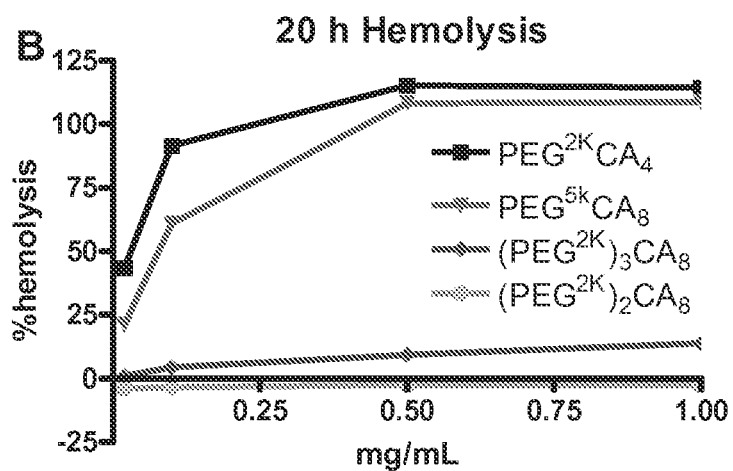

Without being bound by any particular theory, it is hypothesized that the thicker layer of PEG in the outer layer of micelle may be able to stabilize drug loading properties of the micelles. It may also provide sufficient stereo-hindrance to avoid the expose of hydrophobic core of the micelle to the cell membrane, therefore to reduce the hemolysis properties. As shown in FIG. 4, bow-tie shaped polymers 1 and 2 with dendritic oligocholanes and 2-arms or 3-arms of branched PEG (2 KDa), respectively, have been synthesized via solid phase synthesis. Polymer 2 exhibits fairly good paclitaxel (PTX) loading capacity and stability at a drug/polymer ratio of 1:4. The particle sizes of the micelles formed from polymer 1 and polymer 2 were observed to be similar at 24.6 and 19.6 nm, respectively with monodispersed size distribution before drug loading (FIG. 3). After loading with PTX at 1:4 mass ratio of drug to polymer, micelles from polymer 2 remain stable small particle sizes of 28.6 nm by DLS measurements. However, a significant PTX precipitation was observed from the micelles solution formed by polymer 1 at the same condition. Polymer 2 also demonstrated better DOX loading properties. The particle size of the DOX-PEG$^{2K}_3$CA$_8$ (drug/polymer m/m 3:20) was observed to be 15.5 nm by DLS analysis with majority of narrow dispersed small sizes. However, under the same conditions for DOX-PEG$^{2K}_2$CA$_8$ (3:20), significant precipitation was observed and multiple peaks were observed via the DLS analysis at 463 and 1901 nm. As shown in FIG. 5, the bow-tie shaped polymers had very low hemolytic properties even at the highest concentration of 1 mg/mL after 20 hour's incubation.

Example 4. Synthesis of Building Blocks for Telodendrimers

Figure 6:
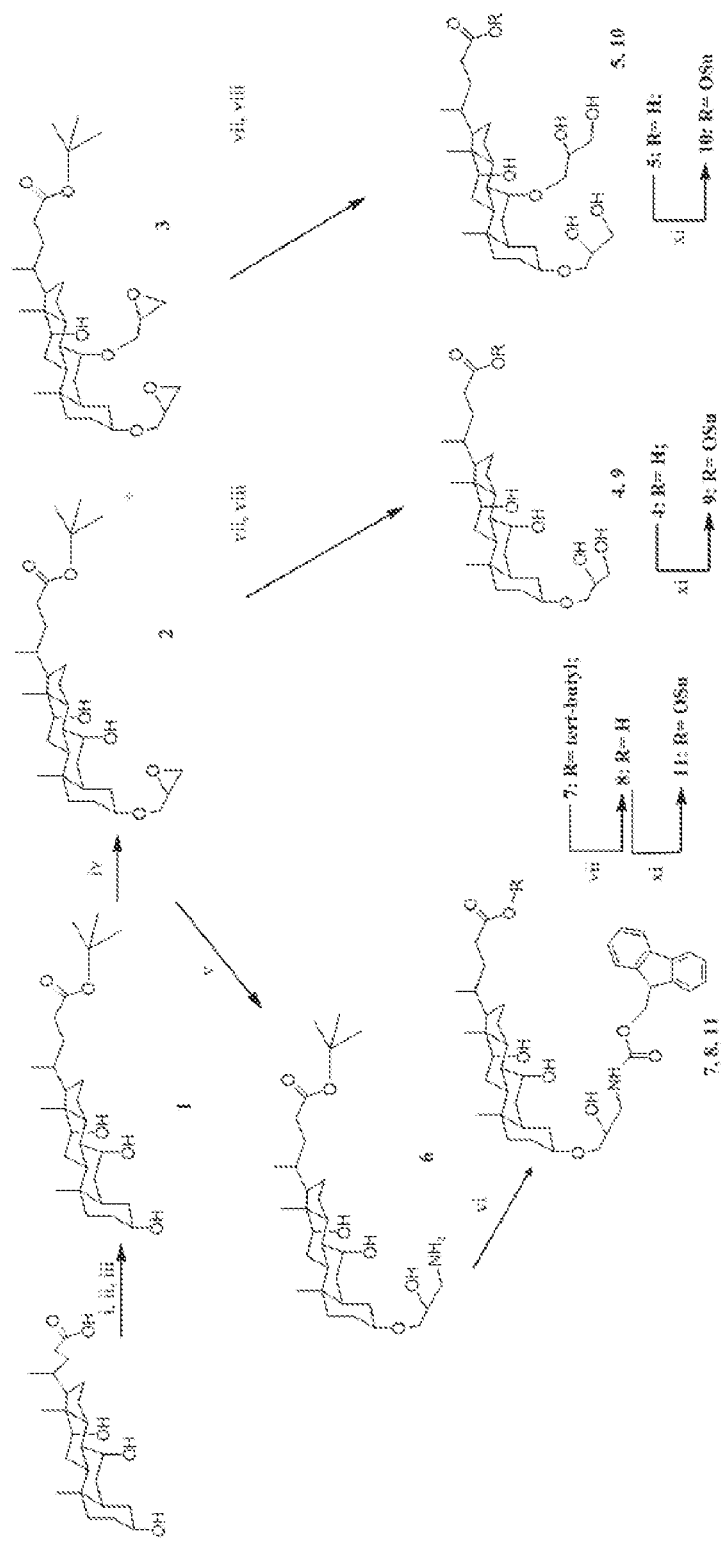
FIG. 6 shows the synthetic scheme for building blocks for telodendrimers. Reagents and conditions: i) TFAA, anhydrous THF, 0~5° C., 1.5 hr; ii) t-BuOH, below 5° C., then at r.t. for 7 hr; iii) NH$_3$.H$_2$O (20~30%), 0~5° C. for 12 hr, then r.t. for 4 hr; iv) Epichlorohydrin, 50% NaOH, (n-Bu)$_4$NOH.30H$_2$O, CH$_2$Cl$_2$, r.t., 16 hr; v) NH$_3$ in MeOH (7 M), LiCl (1.2 eq.) in a sealed container, r.t., 24 hr; vi) Fmoc-OSu (1.2 eq.), DIEA (1.5 eq.), CH$_2$Cl$_2$, 12 hr; vii) 50% TFA in CH$_2$Cl$_2$, 0° C., 30 min; viii) LiOH water solution (10 eq.), r.t., 18~36 hr; xi) SuOH (1.2 eq.), DCC (1.2 eq.), CH$_2$Cl$_2$, r.t., 12 hr.

Cholic acid, an important building block in the telodendrimers, is known to have strong membrane activities as a small molecular surfactant. It has been widely used in for substance transfer through phospholipid bilayer membranes. Without being bound by any particular theory, it is believed that the interaction between the hydrophilic surfaces of cholic acid molecules via hydrogen bonding shelters the polar surfaces of cholic acid via stacking. The hydrophobic surfaces are then exposed for insertion of the cholic acid complexes into the hydrophobic interior of the phospholipid bilayer. Therefore, the disruption of the packing between the hydrophilic surfaces of oligo-cholic acid may reduce the membrane activity of these types of molecules. We have introduced glycerol and aminoglycerol groups at the 3α-OH and 5α-OH groups of cholic acid via ether bond formation to increase the steric hindrance while maintaining the facial amphiphilicity. The synthesis of these derivatives as described below is outlined in FIG. 6.

t-Butyl Cholate (t-Butyl 3α,7α,12α-Trihydroxy-5β-cholan-24-ate) (1)

Trifluoroacetic anhydride (100 mL, 45.07 mmol) was dropped into a stirred solution of cholic acid (25.0 g, 61.24 mmol) dry THF (400 mL) below 0° C. After the ice bath was removed, the solution was stirred for 1.5 hr at room temperature. Then the solution was cooled again, and dry t-BuOH (150 mL) was added below 0° C. After the solution was stirred for 7 hr at room temperature, the first portion of aqueous $NH_3$ (120 ml, 28%, w/w) was dropped into the solution below 5° C. and the solution was stirred for 12 hr at 0~5° C. Then another portion of aqueous $NH_3$ (60 mL) was added into the solution. After a further 4 hr at room temperature, the mixture was partitioned between $Et_2O$ (800 mL) and water (200 mL). After washing with aqueous NaOH (1 M, 800 mL) and water (2×500 mL), the organic layer was dried with anhydrous $MgSO_4$. A foam was obtained after evaporation and a white solid of t-butyl cholate 1 (27.5 g, 96.7%) was obtained by crystallization with acetonitrile (80 mL). MS (m/z) M+H$^+$: Cal. 464.4. Found 465.5.

t-Butyl (3α,5β,7α,12α)-7,12-Dihydroxy-3-(oxyranylmethoxy)-cholan-24-ate (2)

A solution of 1 (25 g, 53.84 mmol) in $CH_2Cl_2$ (15 mL) was added into a mixture of epichlorohydrin (65 mL), aqueous NaOH (50%, w/w, 120 mL) and (n-Bu)$_4$NOH.30H2O (8.0 g, 1 mmol) under vigorous stirring below 20° C. The mixture was stirred for additional 16 hr at room temperature. Two products were verified by TLC method ($R_f$=0.4 and 0.6 in n-hexane/ethyl acetate (1:1, v/v) system). After water (200 mL) was added into the mixture, the organic layer was separated and dried by anhydrous $MgSO_4$ overnight. After the solvent was evaporated, a pink yellow oil was obtained and purified by flash chromatography (n-hexane/EtOAc, 4:1, 2:1 and 1:1, v/v). All the components with their $R_f$>0.4 were collected together for the separation of 3. Compound 2 was obtained as a white foam ($R_f$=0.4 in n-hexane/ethyl acetate 1:1, v/v), 12.5 g, yield 44.7%. HRMS (m/z) M+H$^+$: Cal. 521.3837. Found 521.3839. $^1$H NMR (600 MHz, CDCl$_3$): δ=3.97 (1H, s), 3.83 (1H, s), 3.69 (1H, m), 3.46 (1H, m), 3.18 (1H, s), 3.12 (1H, s), 2.78 (1H, t, J=4.8 Hz), 2.60 (1H, m), 1.43 (9H, s), 1.15~2.23 (23H, m), 0.97 (3H, d, J=6.6 Hz), 0.88 (3H, s), 0.68 (1H, s).

t-Butyl (3α,5β,7α,12α)-12-Dihydroxy-3,7-di(oxyranylmethoxy)-cholan-24-ate or t-Butyl (3α,5β,7α,12α)-7-Dihydroxy-3,12-di(oxyranylmethoxy)-cholan-24-ate (3)

The components with $R_f$>0.4, described above, were separated by flash chromatography (n-hexane/EtOAc, 4:1, 2:1 and 1:1, v/v), and compound 3 was obtained as yellow jelly, 4.5 g, yield 14.5%. HRMS (m/z) M+NH$_4^+$: Cal. 594.4364. Found 594.4375. $^1$H NMR (600 MHz, CDCl3): δ=3.93 (1H, s), 3.81 (1H, s), 3.38~3.52 (4H, m), 3.17 (2H, m), 3.12 (2H, s), 2.78 (2H, m, J=4.2 Hz), 2.59 (2H, m), 1.43 (9H, s), 1.15~2.23 (23H, m), 0.96 (3H, d, J=6.6 Hz), 0.88 (3H, s), 0.67 (1H, d s).

(3α,5β,7α,12α)-7,12-Dihydroxy-3-(2,3-dihydroxy-1-propoxy)-cholic acid (4)

$CF_3COOH$ (25 mL) was dropped into the solution of 2 (1.6 g, 3.07 mmol) in $CH_2Cl_2$ (25 mL) below 0° C. under stirring. The mixture was stirred for another 1.5 hr at room temperature. TLC (n-hexane/EtOAc, 1:1, v/v) confirmed that the reaction was completed. After the solvents were removed by air blowing, a yellow jelly was obtained. LiOH (0.7 g, 10 eq.) in aqueous solution (20 mL) was added into the flask. The residue disappeared gradually and a pink yellow solution was obtained. After stirred at room temperature for 16 hr, the solution was cooled below 5° C. and condensed HCl was dropped into the solution. Compound 4 precipitated out as white solid, and TLC test confirmed that product was pure and could be used in the next step without further purification. After lyophilization, 4 (1.25 g) was obtained, yield 84.4%. HRMS (m/z) M+H$^+$: Cal. 483.3317. Found 483.3315. $^1$H NMR (600 MHz, DMSO-d6): δ=5.58 (1H, ds), 4.14 (1H, s), 4.03 (2H, m), 3.79 (1H, m), 3.74 (1H, s), 3.61 (1H, s), 3.50 (1H, m), 3.20 (1H, m), 3.02 (1H, m), 2.76 (1H, s), 2.67 (1H, m), 2.59 (2H, m), 1.15~2.24 (23H, m), 0.96 (3H, d, J=6.6 Hz), 0.82 (3H, s), 0.60 (3H, s).

(3α,5β,7α,12α)-12-Dihydroxy-3,7-di(2,3-dihydroxy-1-propoxy)-cholic acid or t (3α,5β,7α,12α)-7-Dihydroxy-3,12-di(2,3-dihydroxy-1-propoxy)-cholic acid (5)

$CF_3COOH$ (30 mL) was dropped into the solution of Compound 3 (3.5 g, 6.01 mmol) in $CH_2Cl_2$ (30 mL) below 0° C. under stirring. The mixture was stirred for another 2.5 hr at room temperature. After the solvents removed by air blowing, a yellow jelly was obtained. LiOH (2.0 g, 20 eq.) in aqueous solution (25 mL) was added into the flask. The residue disappeared gradually and a pink yellow solution was obtained. After stirring at room temperature for 16 hr, the solution was cooled below 5° C. and condensed HCl was dropped into the solution. The product was extracted with 3×100 mL ethyl acetate and the organic layer was dried with anhydrous $Na_2SO_4$. After purification by flash chromatography ($CH_2Cl_2$:$CH_3OH$=5:1, 3:1, v/v), compound 5 was obtained as pink yellow jelly, 1.22 g, yield 36.5%. HRMS (m/z) M+H$^+$: Cal. 557.3684. Found 557.3682. $^1$H NMR (600 MHz, DMSO-d6): δ=4.56 (1H, s), 4.46 (2H, s), 3.77 (1H, s), 3.50 (4H, m), 3.27 (2H, m), 3.16 (4H, m), 3.00 (2H, m), 2.50 (3H, m), 2.46 (1H, s), 1.17~2.25 (23H, m), 0.87~0.92 (3H, m), 0.83 (3H, s), 0.58~0.62 (3H, ds).

t-Butyl (3α,5β,7α,12α)-7,12-Dihydroxy-3-(3-amino-2-hydroxy-1-propoxy)-cholan-24-ate (6)

Compound 2 (6.5 g, 12.49 mmol) was dissolved into $NH_3$ methanol solution (7M, 150 mL) containing LiCl (0.4 g, mmol, eq.) in a sealed flask and stirred at room temperature for 24 hr. TLC test ($R_f$=0.3, $CH_2Cl_2$:MeOH:$NH_3$.H2O (25%)=10:1:0.1, v/v/v) proved the reaction was completed. After purification by flash chromatography ($CH_2Cl_2$:MeOH:$NH_3$.H2O (25%)=10:1:0.1, v/v/v), compound 6 was obtained as white foam, 6.2 g, yield 92.4%. HRMS (m/z) M+H$^+$: Cal. 538.4102. Found 538.4099. $^1$H NMR (600 MHz, CDCl$_3$): δ=3.95 (1H, s), 3.83 (1H, s), 3.76 (1H, s), 3.50 (1H, m), 3.43 (1H, m), 3.12 (1H, m), 2.83 (1H, m), 2.75 (2H, m), 2.64 (3H, s), 1.43 (9H, s) 1.12~2.29 (23H, m), 0.97 (3H, d, J=6.6 Hz), 0.88 (3H, s), 0.67 (3H, s).

t-Butyl (3α,5β,7α,12α)-7,12-Dihydroxy-3-(3-Fmocamino-2-hydroxy-1-propoxy)-cholan-24-ate (7)

Compound 6 (3.0 g, 5.58 mmol), Fmoc-OSu (3.0 g, 8.90 mmol) and DIEA (1.5 g, 11.61 mmol,) were dissolved into $CH_2Cl_2$ (100 mL) and stirred at room temperature for 16 hr. TLC test (Ethyl acetate/Hexane=5:2, v/v) proved there was no starting material left. After the solvent was removed at reduced pressure, the residue was purified by flash chromatography (Ethyl acetate/Hexane=5:2, v/v, $R_f$=0.3). Compound 7 was obtained as white foam, 4.1 g, yield 96.8%.

HRMS (m/z) M+H+: Cal. 760.4783. Found 760.4795. $^1$H NMR (600 MHz, CDCl$_3$): δ=7.30~7.76 (8H, m), 5.41 (1H, m), 4.39 (2H, d, J=7.2 Hz), 4.20 (1H, t, J=7.2 Hz), 4.12 (1H, m), 3.96 (1H, s), 3.83 (2H, s), 3.51 (1H, m), 3.39 (2H, m), 3.20 (1H, m), 3.12 (1H, m), 1.43 (9H, s), 1.12~2.30 (23H, m), 0.96 (3H, d, J=6.6 Hz), 0.88 (3H, s), 0.68 (3H, s).

(3α,5β,7α,12α)-7,12-Dihydroxy-3-(3-Fmocamino-2-hydroxy-1-propoxy)-cholic acid (8)

CF$_3$COOH (100 mL) was dropped into the solution of compound 8 (11.0 g, 14.48 mmol) in CH$_2$Cl$_2$ (100 mL) under stirring below 0° C. The mixture was stirred at room temperature for another 4.5 hr. After the solvents were removed by air blowing, the residue was dissolved into CH$_2$Cl$_2$ (300 mL) and washed with 3×100 mL water. After dried with anhydrous Na$_2$SO4 overnight, the organic layer was evaporated under reduced pressure. A pink yellow jelly was obtained and purified by flash chromatography (Ethyl acetate/CH$_3$OH=20:1, v/v, R$_f$=0.3). Compound 8 was obtained as white foam, 9.0 g, yield 88.40%. HRMS (m/z) M+H+: Cal. 704.4157. Found 704.4162. $^1$H NMR (600 MHz, CDCl$_3$): δ=7.28~7.75 (8H, m), 5.60 (1H, s), 4.38 (2H, d, J=7.2 Hz), 4.20 (1H, t, J=7.2 Hz), 4.11 (2H, m), 3.95 (1H, s), 3.85 (1H, s), 3.82 (1H, s), 3.61 (1H, s), 3.49 (1H, m), 3.39 (2H, m), 3.11 (1H, s), 3.10 (1H, m), 1.15~2.37 (23H, m), 1.08 (1H, m) 0.98 (3H, d, J=6.6 Hz), 0.87 (3H, s), 0.66 (3H, s).

Succinimidyl Esters of Cholic Acid Derivatives (9, 10, 11)

Compound 4, 5, or 8 was dissolved into CH$_2$Cl$_2$ containing SuOH (1.2 eq.) and DCC (1.2 eq.), and the mixture was stirred at room temperature for 16 hr. The white precipitate (DCU) was filtered off and the filtrate was condensed under reduced pressure until white foam appeared. After the foam dissolved in ethyl acetate, the solution was allowed to stand overnight at 4° C. for the precipitation of DCU. After the DCU was filtered off, the filtrate was condensed again. The obtained products were used directly for coupling without further purification.

Figure 7:
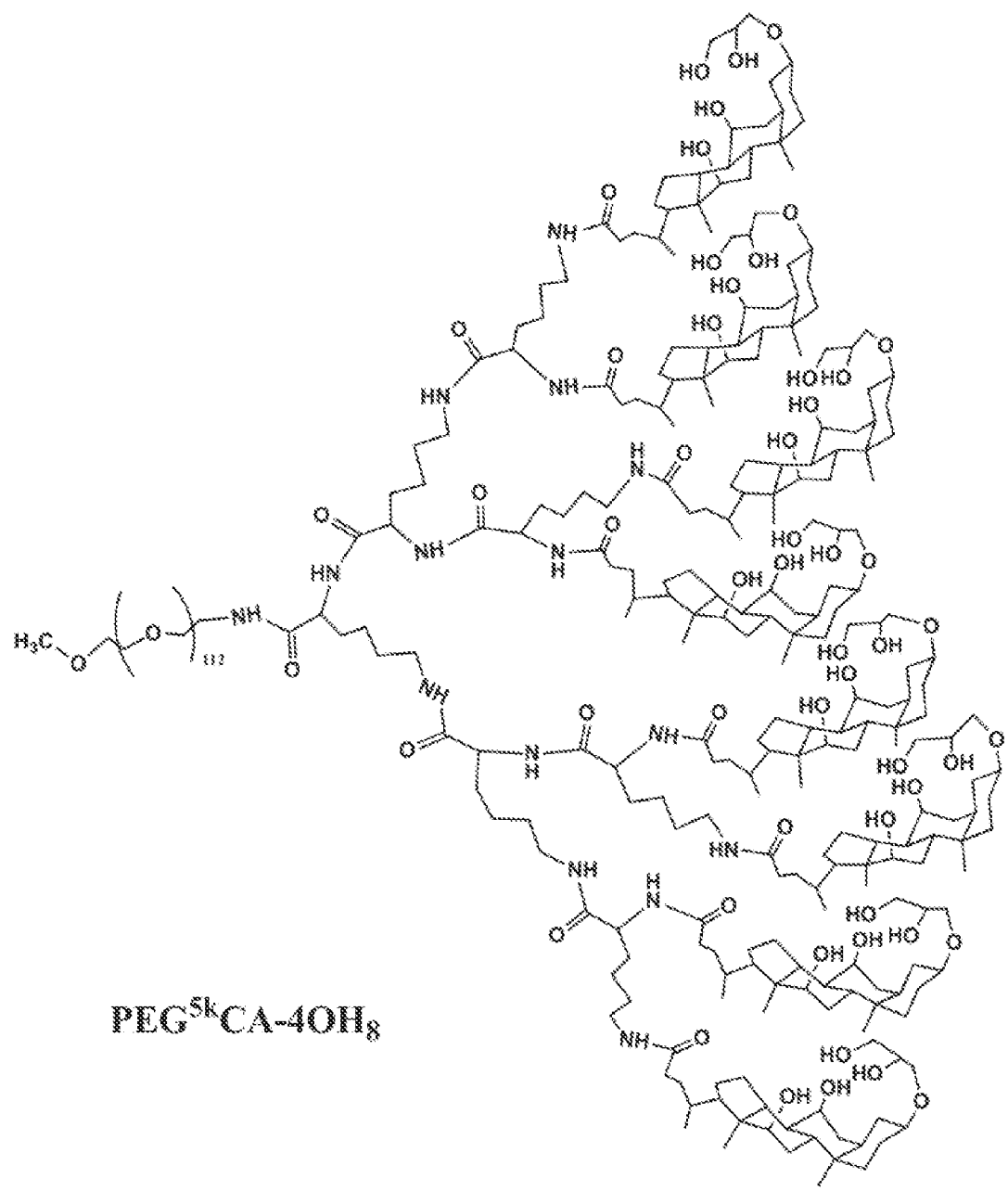
FIG. 7 shows the chemical structure of telodendrimer PEG5kCA-4OH8 using 3-glycerol cholic acid as a building block.
Figure 8:
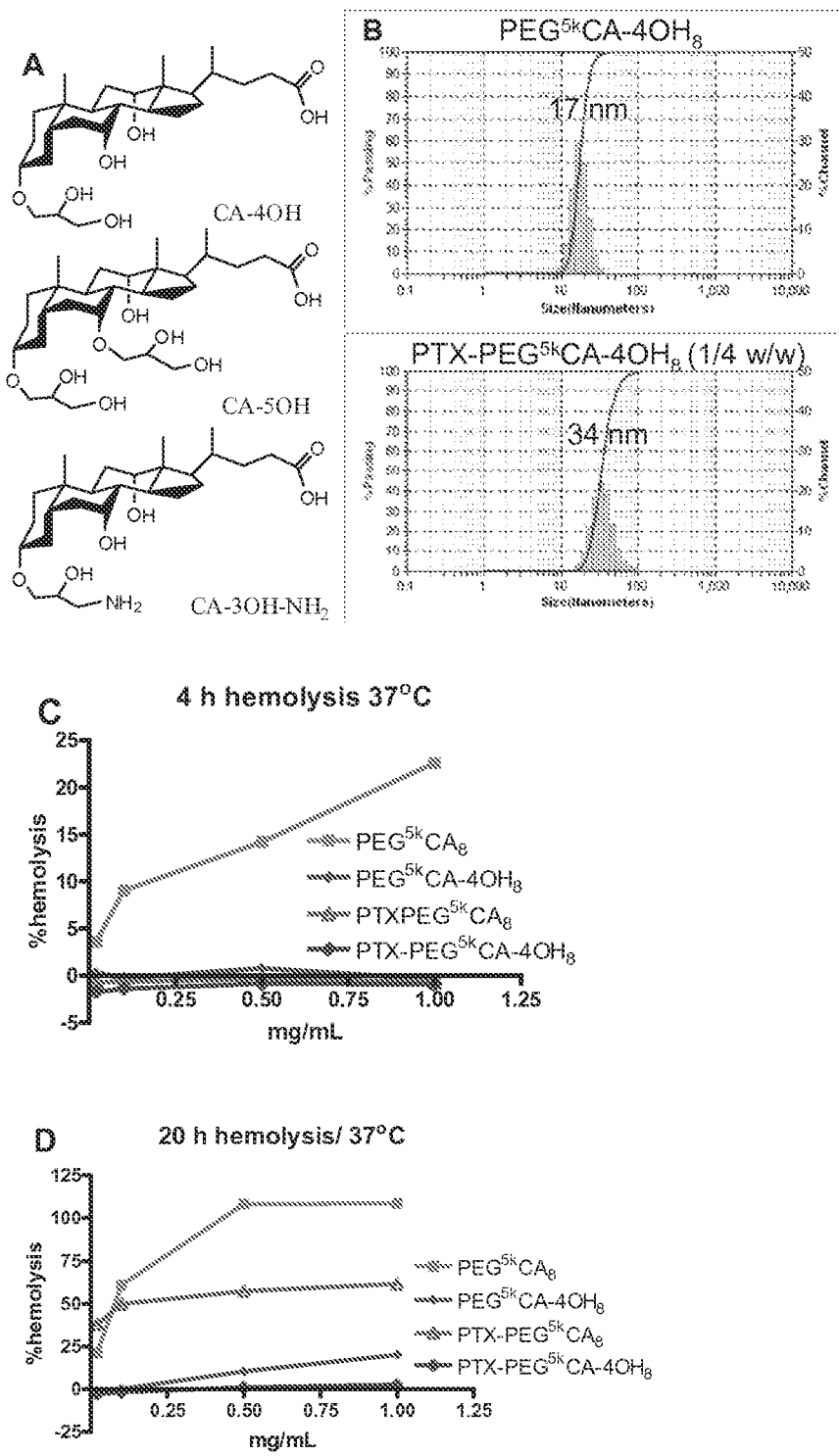
FIG. 8 shows the structures and properties of cholic acid telodendrimers. (A) The chemical structure of the modified cholic acid derivatives with different functional groups; (B) the DLS particle sizes of the telodendrimer PEG$^{5k}$CA-4OH$_8$ micelles before and after PTX loading; (C-D) the hemolytic properties of the telodendrimers PEG$^{5k}$CA-4OH$_8$ before and after PTX loading in comparison with PEG$^{5k}$CA$_8$ at different concentrations and different incubation times.

Preparation of Telodendrimers Containing Cholic Acid Derivatives as Building Blocks We have further synthesized the telodendrimers (FIG. 7) using these derivatized cholic acids as building blocks, instead of cholic acid. Among them, the telodendrimer PEG$^{5k}$CA-4OH$_8$ showed similar PTX loading capacity and stability with the original telodendrimer PEG$^{5k}$CA$_8$. It has the mono-dispersed particle sizes of 17 nm and 34 nm before and after PTX loading (1:4 polymer/drug, w/w, respectively (FIG. 8B). The hemolytic properties of the engineered PEG$^{5k}$CA-4OH$_8$ micelles were observed to be negligible compared with those of PEG$^{5k}$CA$_8$ (FIG. 8C-D) after 4 h or 20 h incubation at 37° C. with red blood cells. After loading with PTX, PEG$^{5k}$CA-4OH$_8$ micelles were observed to be non-hemolytic up to 1 mg/mL after 20 h incubation, whereas 100% and 50% hemolysis were caused by the original telodendrimer PEG$^{5k}$CA$_8$ before and after PTX loading, respectively, under the same conditions.

Example 5. Synthesis of Hybrid Telodendrimers

Given a polymer micelle system, the affinity between drug molecules and polymer backbone determines the drug loading capacity and stability of the micelles. PTX, for example, has shown excellent loading capacity and stability in the telodendrimer micelles such as PEG$^{5k}$CA$_8$ and PEG$^{2k}$CA$_4$. We hypothesize that the introduction of other drug-like molecules (DLM) as building blocks in the telodendrimer will endow the micelles with strong affinities for a variety of drug cargoes via multiple interactions, such as hydrophobic interaction, π-π interaction, hydrogen bonding and possible ionic interactions. We have conjugated Rhein (Rh) and cholic acid into hybrid telodendrimers via an orthogonal Boc-Fmoc protection strategy. Rhein (Rh) is a major bioactive component in rhubarb (Dahuang), a traditional Chinese medicine derived from the rhizome of Rheum palmalunm and related species. It is reported to have antitumor and anti-inflammation properties. It is a biocompatible natural compound processing a similar anthracycline structure with the DOX.

Materials

Doxorubicin hydrochloride (DOX.HCl) (Novaplus) and Doxil® (Ben Venue Laboratories, Inc., Bedford, Ohio) were obtained from the UC Davis Cancer Center Pharmacy. Monomethyl-terminated poly(ethylene glycol)monoamine (MeO-PEG-NH$_2$, Mw=5 kDa) were purchased from Rapp Polymere (Tuebingen, Germany). (Fmoc)Lys(Boc)-OH, (Fmoc)Lys(Dde)-OH, (Fmoc)Lys(Fmoc)-OH were obtained from AnaSpec Inc. (San Jose, Calif.). Tetrazolium compound [3-(4,5-dimethylthiazol-2-yl)-5-(3-carboxymethoxyphenyl)-2-(4-sulfophenyl)-2H-tetrazolium, MTS] and phenazinemethosulfate (PMS) were purchased from Promega (Madison, Wis.). Rhein, cholic acid, triethylamine (TEA), and all other chemicals were purchased from Sigma-Aldrich (St. Louis).

Synthesis of Engineered Telodendrimers (PEG$^{10k}$CONH-DOX$_4$, PEG$^{10k}$-N=C-DOX$_4$, PEG$^{5k}$-Rh$_8$) and Hybrid Telodendrimers (PEG$^{5k}$-CA$_4^\alpha$CF$_4^\epsilon$; PEG$^{5k}$-CA$_4^\alpha$CA$_4^\epsilon$; PEG$^{5k}$-CA$_4^\alpha$Rh$_4^\epsilon$, PEG$^{5k}$-Rh$_4^\alpha$CA4$^\epsilon$)

The telodendrimers were synthesized via solution-phase condensation reactions using MeO-PEG-NH$_2$, lysine and cholic acid as building blocks. Briefly, Fmoc peptide chemistry was used to couple (Fmoc)Lys(Fmoc)-OH onto the N-terminus of PEG (MW=5 or 10 kDa) using diisopropylcarbodiimide (DIC, 3 equiv) and N-hydroxybenzotriazole (HOBt, 3 equiv) as coupling reagents in DMF overnight. Upon the negative Kaiser test of the reaction, the chilled ether was added to the reaction solution to precipitate the polymer, which was further washed twice with chilled ether. Fmoc protecting groups were removed by the treatment with 20% piperidine in DMF for 30 min. Polymer was precipitated and washed with chilled ether.

PEG$^{5k}$-Rh$_8$ synthesis: third-generation dendritic polylysine was synthesized via three repeated (Fmoc)Lys(Fmoc)-OH couplings to MeO-PEG-NH$_2$ as mentioned above. At the end, the polylysine was capped with Rhein via HOBt/DIC coupling chemistry.

PEG$^{10k}$CONH-DOX$_4$ synthesis: second-generation dendritic polylysine was treated with excess succinic anhydride (5 equivalents to NH$_2$) to generate carboxylic acid groups. Further, doxorubicin was coupled onto COOH groups on the secondary generation of dendron via DIC/HOBt condensation reaction in the presence of DIEA.

PEG$^{10k}$N=C-DOX$_4$ synthesis: the second-generation carboxylic acid-functionalized dendrimer, prepared as above, was reacted with HOSu using DIC as a coupling reagent. The active NHS ester was further treated with excess of hydrazine in DMF. At the end the poly-acyl hydrazine reacted with doxorubicin in the presence of TFA as catalyst. The acid labile acyl hydrazone linkages were generated for DOX conjugation. The telodendrimers were precipitated and washed three times with cold ether, dialyzed against water in a dialysis tube with molecular weight cutoff (MWCO) of 3.5 kDa for 24 h and then lyophilized.

Hybrid telodendrimer synthesis: Second-generation dendritic polylysine was synthesized via two repeated cycles of (Fmoc)Lys(Fmoc)-OH coupling to MeO-PEG-NH$_2$. (Fmoc)Lys(Boc)-OH was coupled onto the second generation of dendritic polylysine via DIC/HOBt chemistry. The Fmoc group was removed by the treatment with 20% piperidine in DMF, followed by the coupling of Rhein (Rh), Cholesterol chloroformate (CF) or cholic acid (CA) onto the α position of lysine. Then Boc protecting groups were removed by the 50% TFA in DCM for 30 min. Then CA, Rh, or CF reacted, respectively, with the ε position of lysine to generate hybrid telodendrimers. The telodendrimers were precipitated and washed three times with cold ether, dialyzed against water in a dialysis tube with molecular weight cutoff (MWCO) of 3.5 kDa for 24 h and then lyophilized. The molecular weight of the telodendrimer was characterized using MALDI-TOF mass spectrometry Preparation and Characterization of DOX-Loaded Rhein-Containing Telodendrimer Micelles DOX-loaded PEG$^{5k}$-CA$_4$$^α$Rh$_4$$^ε$ micelles were prepared via a dry-down (evaporation) method. Before the encapsulation of DOX into the polymeric micelles, DOX.HCl was stirred with 3 molar equivalent of triethylamine in chloroform (CHCl$_3$)/methanol (MeOH) (1:1, v/v) overnight to remove HCl from DOX.HCl. 20 mg PEG$^{5k}$-CA$_4$$^α$Rh$_4$$^ε$ telodendrimer along with different amounts of neutralized DOX were first dissolved in CHCl$_3$/MeOH, mixed, and evaporated on rotavapor to obtain a homogeneous dry polymer film. The film was reconstituted in 1 mL phosphate buffered solution (PBS), followed by sonication for 30 min, allowing the sample film to disperse into micelle solution.

The particle size distribution of DOX-PEG$^{5k}$-CA$_4$$^α$Rh$_4$$^ε$ micelles were characterized by dynamic light scattering (DLS, Microtrac). The stability of DOX-loaded micelles upon storage was evaluated by monitoring the particle sizes of micelles using DLS. The PEG$^{5k}$-CA$_4$$^α$Rh$_4$$^ε$ and DOX-PEG$^{5k}$-CA$_4$$^α$Rh$_4$$^ε$ micelles were characterized via proton NMR both in deuterated chloroform and water.

Cell Culture and Animals

T-cell lymphoma cell lines (Jurkat and MOLT-4) and B-cell lymphoma cell lines (Raji and Ramos) were purchased from American Type Culture Collection (ATCC); Manassas, Va., USA). All these cells were cultured in ATCC-formulated RPMI-1640 medium supplemented with 10% fetal bovine serum (FBS), 100 U/mL penicillin G, and 100 µg/mL streptomycin at 37° C. using a humidified 5% CO$_2$ incubator.

Female SPF BALB/c mice, 8-10 weeks age, were purchased from Charles River (Hollister, Calif.): female athymic nude mice (Nu/Nu strain), 6-8 weeks age, were purchased from Harlan (Livermore, Calif.). All animals were kept under pathogen-free conditions according to AAALAC (Association for Assessment and Accreditation of Laboratory Animal Care) guidelines and were allowed to acclimatize for at least 4 days prior to any experiments. All animal experiments were performed in compliance with institutional guidelines and according to protocol No. 07-13119 and No. 09-15584 approved by the Animal Use and Care Administrative Advisory Committee at the University of California, Davis. Lymphoma xenograft mouse models were established by subcutaneously injecting 1×10$^7$ Raji lymphoma cells in a 100 µL of mixture of PBS and Matrigel (1:1 v/v) at the right flank in female nude mice.

In Vitro Cytotoxicity Assay

The MTS assay was used to evaluate the effects of DOX-loaded micellar NPs on the cell viability against both T and B lymphoma cell lines. MOLT-4, Jurkat, Raji and Ramos cells were seeded in 96-well plates at cell densities of 4×10$^3$ cells/well. After overnight incubation, the cells were treated with different concentrations of DOX.HCl, Doxil®, and DOX-loaded micelle, as well as the equivalent dose of blank micelles. After 72 h incubation, CellTiter 96® Aqueous Cell Proliferation Reagent, which is composed of MTS and an electron coupling reagent PMS, was added to each well according to the manufacturer's instructions. The cell viability was determined by measuring the absorbance at 490 nm using a microplate reader (SpectraMax M2, Molecular Devices. USA). Untreated cells served as a control. Results are calculated and discussed as the average cell viability [(OD$_{treat}$−OD$_{blank}$)/(OD$_{control}$1−OD$_{blank}$)×100%] of triplicate wells.

Maximum Tolerated Dose (MTD) Studies

Healthy female SPF BALB/c mice were administered intravenously with DOX.HCl or DOX-PEG$^{5k}$-CA$_4$$^α$Rh$_4$$^ε$ (3 mg/ml DOX in 20 mg/ml telodendrimer) at the dose of 5, 10, 15 and 20 mg DOX/kg body weight, respectively (n=4). Mice survival and body weight change were monitored daily for two weeks. At one week after injection, the blood was collected from each mouse to measure blood cell counts and serum chemistry including alanine aminotransferase (ALT), aspartate aminotransferase (AST), total bilirubin (TB), blood urea nitrogen (BUN) and creatine. The MTD was defined as the allowance of a median body weight loss of 15% and causes neither death due to toxic effects nor remarkable changes in the general signs within two weeks after administration.

In Vivo Anti-Tumor Efficacy Study

Subcutaneous Raji lymphoma xenograft mouse model was used to evaluate the therapeutic efficacy of different formulations of DOX. When tumor volume reached 150-300 mm$^3$, mice were intravenously administrated with PBS, DOX.HCl, Doxil®, or DOX-PEG$^{5k}$-CA$_4$$^α$Rh$_4$$^ε$ at the dose of 10 mg/kg DOX equivalent (MTD of free DOX) (n=5-8). The treatment was given every four day on days 0, 4 and 8 for total three doses. Tumor sizes were measured with a digital caliper twice per week. Tumor volume was calculated by the formula (L×W$^2$)/2, where L is the longest, and W is the shortest in tumor diameters (mm). To compare between groups, relative tumor volume (RTV) was calculated at each measurement time point (where RTV equals the tumor volume at given time point divided by the tumor volume prior to initial treatment). For humane reasons, animals were sacrificed when the implanted tumor volume reached 2000 mm$^3$, which was considered as the end point of survival data. At day 7 after the last dosage, blood samples were obtained from all the mice for the measurement of blood cell counts, hepatic or renal function tests (ALT, AST, and BUN), and serum enzyme markers of cardiotoxicity including creatine kinase (CK) and lactate dehydrogenase (LDH). One mouse from each group was also sacrificed, and its heart was submitted for histopathology evaluation.

Statistical Analysis

The level of significance in all statistical analyses was set at a probability of P<0.05. Data are presented as means±standard error (SEM). Statistical analysis was performed by Student's t-test for comparison of two groups, and one-way analysis of variance (ANOVA) for multiple groups, followed by Newman-Keuls test if overall P<0.05.

Results and Discussion

Figure 9:
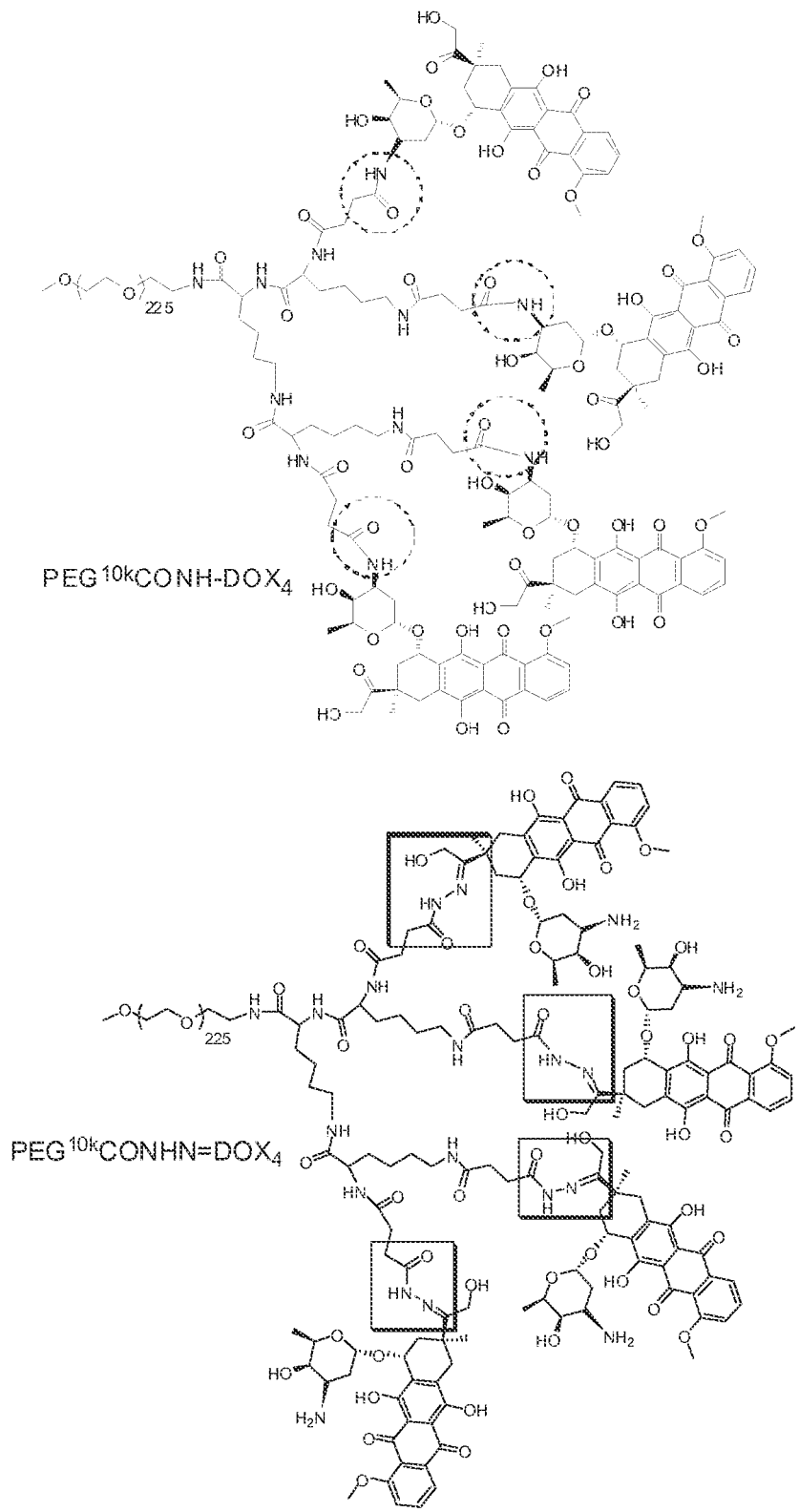
FIG. 9 shows the structures of engineered and hybrid telodendrimers PEG$^{10k}$CONH-DOX$_4$, PEG$^{10k}$CONHN=DOX$_4$, PEG$^{5k}$-Rh$_8$, PEG$^{5k}$-CA$_4$CF$_4$, PEG$^{5k}$-Rh$_4^\alpha$CA$_4^\varepsilon$ and PEG$^{5k}$-CA$_4^\alpha$Rh$_4^\varepsilon$.
Figure 9:
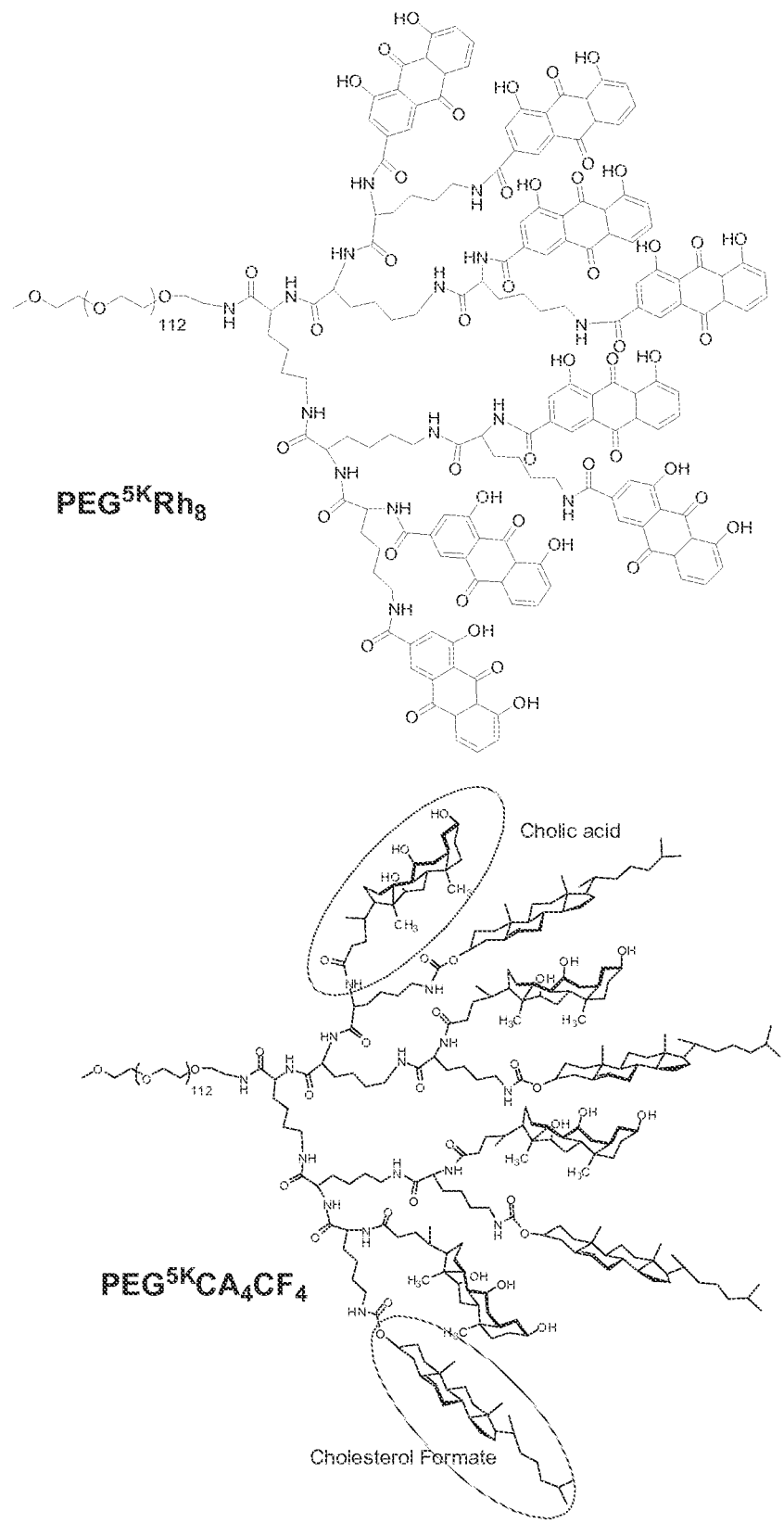
Figure 9:
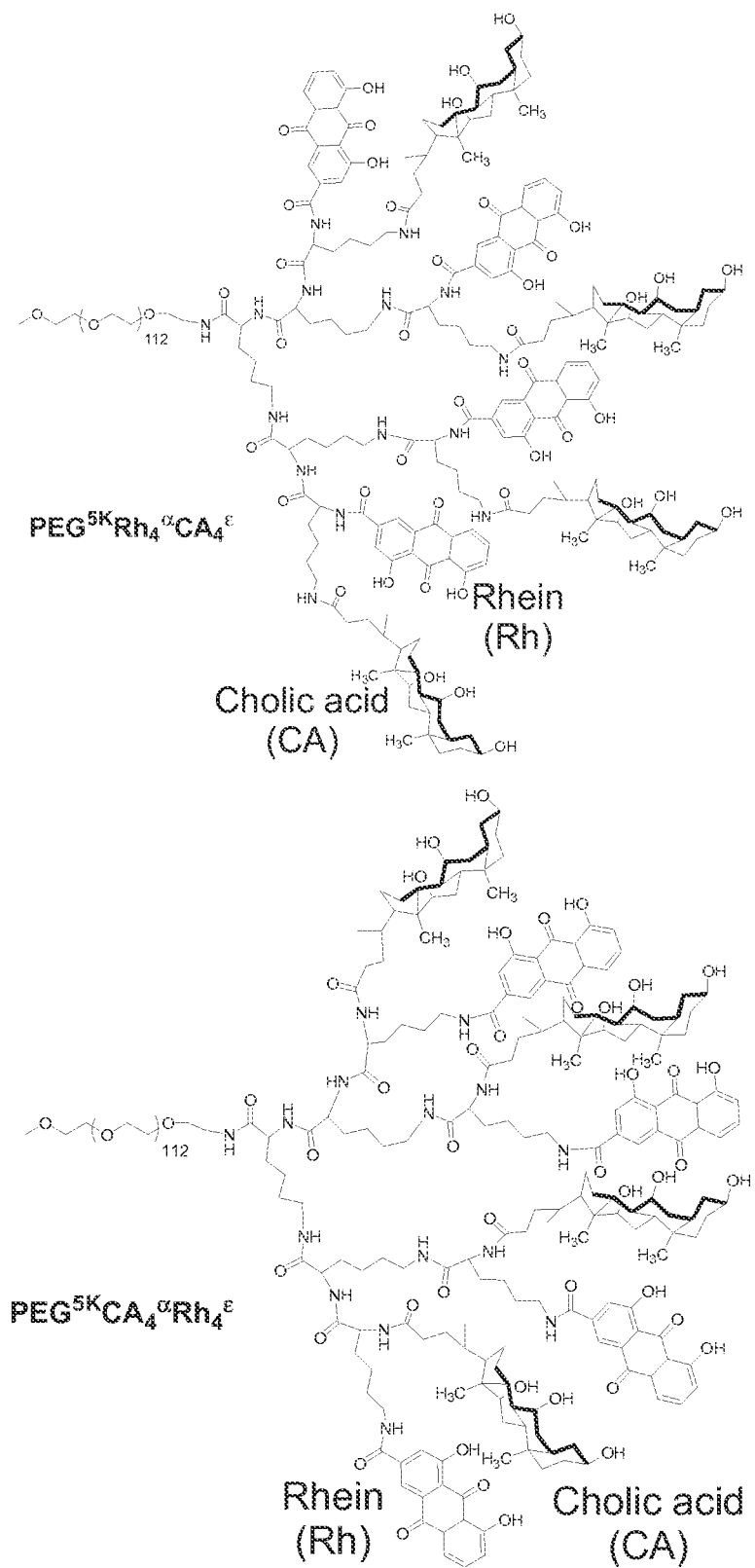

The engineered and hybrid telodendrimers (FIG. 9) have been synthesized via solution phase peptide chemistry using different core-forming building blocks, such as DOX, rhein and cholesterol, solely or in combination with cholic acid. The DOX containing telodendrimers with different chemistry have different sizes after assembly into micelles in aqueous solution, due to the difference of hydrophobicity of DOX residues. Telodendrimer $PEG^{10k}$-N=C-$DOX_4$ have smaller micelle sizes (3.5 nm) than that of $PEG^{10k}$CONH-$DOX_4$ (19.5 nm) which lost a polar $NH_2$ group during DOX conjugation. However, after encapsulation of extra DOX in the $PEG^{10k}$-N=C-$DOX_4$ micelles, the size of the micelles increased to 42 nm with narrow and mono-dispersed size distribution. $PEG^{5k}$-$CA_4^\alpha CF_4^\epsilon$ has a narrowly dispersed particles size after self-assembly in water (30-50 nm). It has been proven to efficiently encapsulate SN-38 to 1.5 mg/mL (drug/telodendrimer m/m 1.5:20) with mono-dispersed particle sizes about 120 nm.

Figure 10:
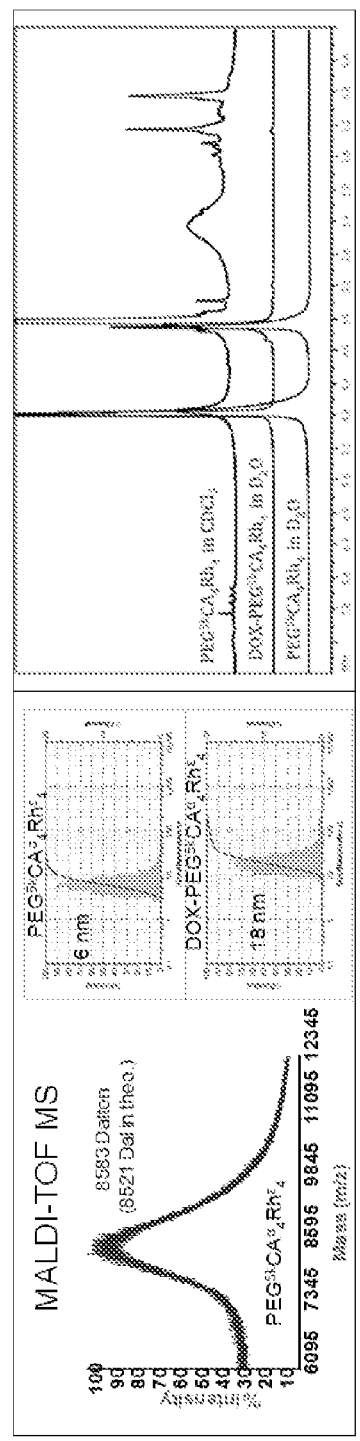
FIG. 10 shows the characterization of PEG$^{5k}$-CA$_4^\alpha$Rh$_4^\varepsilon$ telodendrimers. The MALDI-TOF MS spectrum of PEG$^{5k}$-CA$_4^\alpha$Rh$_4^\varepsilon$ reveals the well defined structure; the DLS particle sizes analysis showed the narrow dispersed particle sizes before and after PTX loading; the proton NMR spectra in D$_2$O show the significant suppressed signals for the core structures of PEG$^{5k}$-CA$_4^\alpha$Rh$_4^\varepsilon$ and the DOX-PEG$^{5k}$-CA$_4^\alpha$Rh$_4^\varepsilon$ indicating the tight core structure formation in the micelle.
Figure 11:
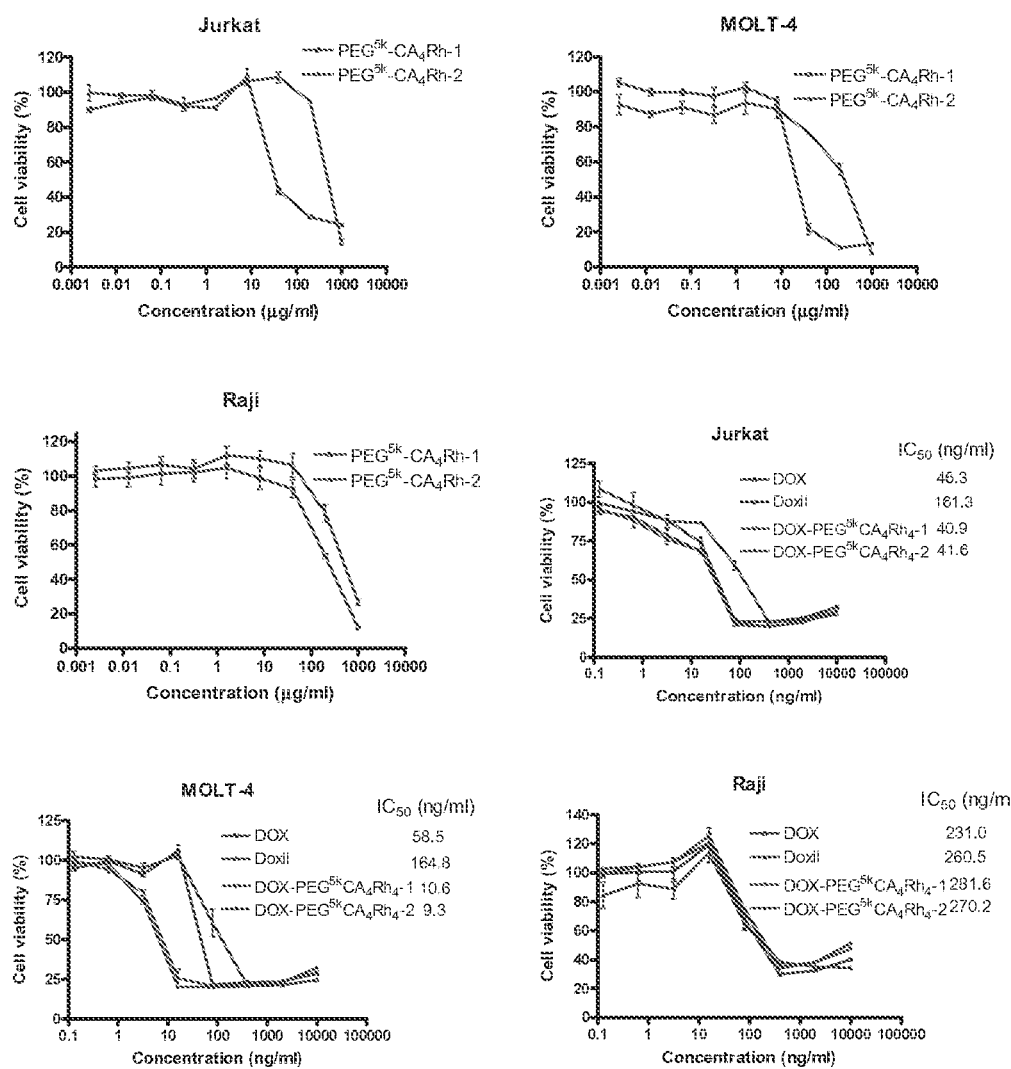
FIG. 11 shows the cytotoxicity of hybrid PEG$^{5k}$-CA$_4^\alpha$Rh$_4^\varepsilon$ telodendrimers before and after DOX loading against three lymphoma cell lines in cell culture.
Figure 12:
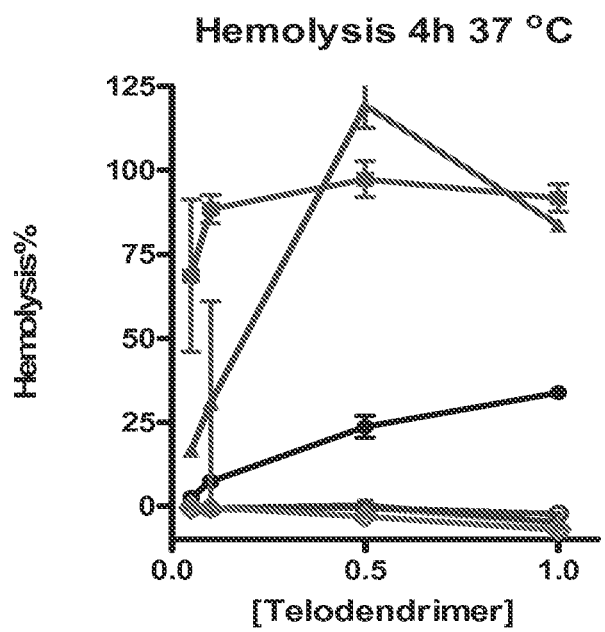
FIG. 12 shows the hemolysis properties of PEG$^{5k}$-CA$_4^\alpha$Rh$_4^\varepsilon$ micelles after incubation for different time (A, 4 h; B, 20 h), compared with other telodendrimer formulations. PEG$^{5k}$-CA$_4^\alpha$Rh$_4^\varepsilon$ do not show any observable hemolysis before and after DOX loading, however, typical telodendrimers showed significant hemolysis even at earlier time point (4 h).
Figure 12:
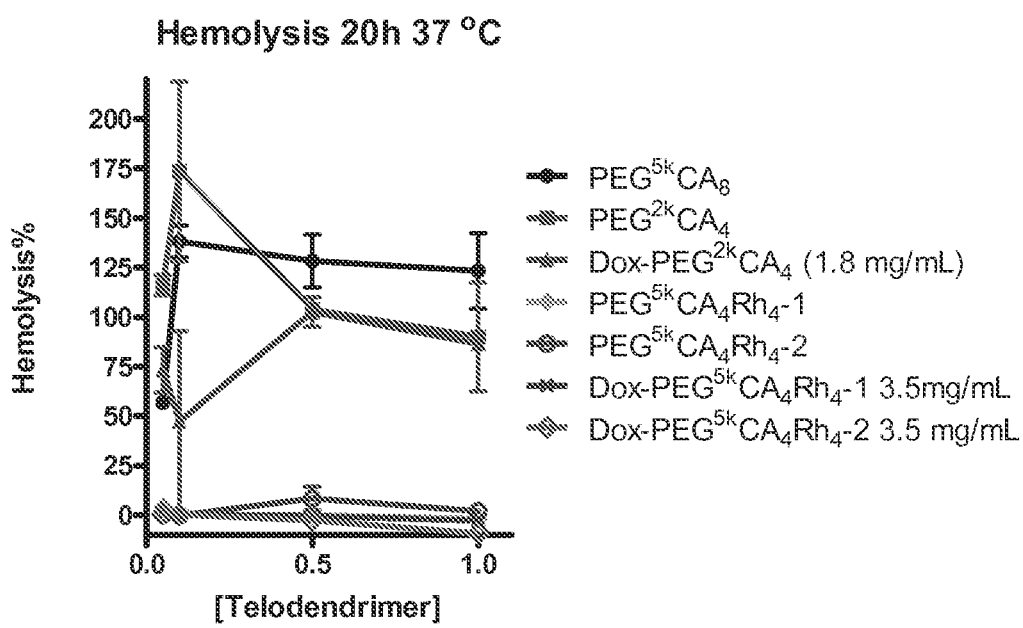
Figure 13:
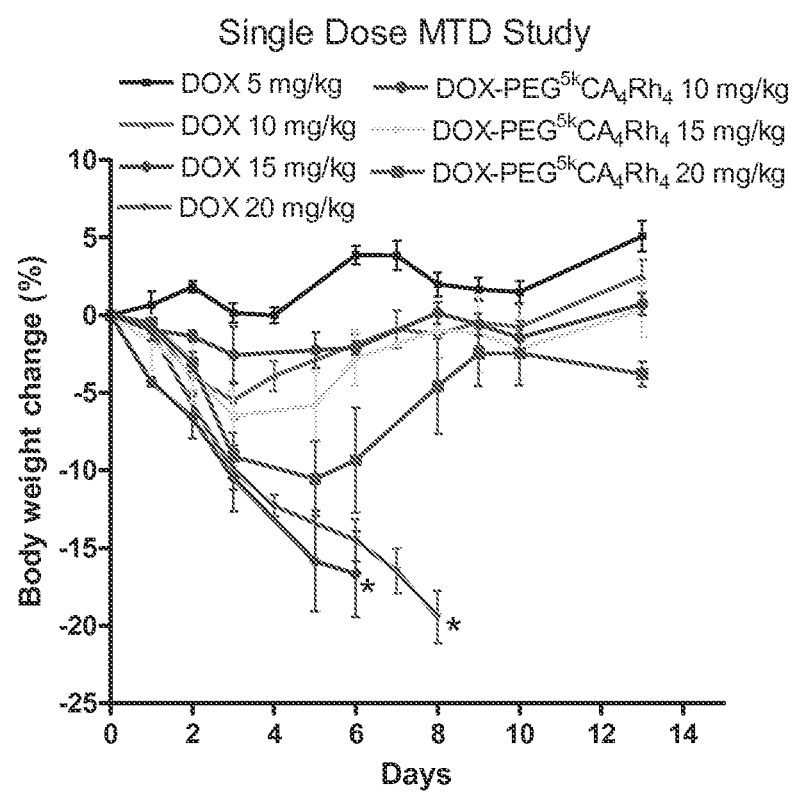
FIG. 13 shows the body weight change of normal BALB/c mice (n=4) administered intravenously with equivalent doses of free DOX or DOX-PEG$^{5k}$-CA$_4^\alpha$Rh$_4^\varepsilon$ micelles in the MTD study.

The well-defined structure of $PEG^{5k}$-$CA_4^\alpha CF_4^\epsilon$ was determined by MALDI-TOF MS with the identical molecular weight to the theoretical value (FIG. 10—left). $PEG^{5k}$-$CA_4^\alpha CF_4^\epsilon$ can load up to 4 mg/mL of DOX (20%/w/w) with 100% loading efficiency. The particles sizes before and after DOX loading was measured by DLS to be 6 nm and 18 nm with narrowly dispersed size distribution (FIG. 10—middle). As shown in FIG. 10—right, the proton NMR spectra of $PEG^{5k}$-$CA_4^\alpha CF_4^\epsilon$ and the DOX loaded micelles in $D_2O$ showed that the signals of the core structures (cholane and Rhein), as well as DOX drug molecules were completed suppressed, indicating the stable solid-like micelle core formation. The particle sizes of the DOX loaded micelles were monitored via DLS to be stable over months (>2 months) without any precipitation at 4° C. and room temperature. The empty $PEG^{5k}$-$CA_4^\alpha CF_4^\epsilon$ micelles were observed to be nontoxic up to few hundreds μg/mL to three lymphoma cell lines (FIG. 11). The DOX loaded $PEG^{5k}$-$CA_4^\alpha CF_4^\epsilon$ micelles showed a similar IC50 value to free DOX and Doxil in some lymphoma cell lines in cell culture, such as Jurkat and Raji cell lines. It was interesting to observe the increased IC50 for Molt-4 cells compared with other DOX formulations (FIG. 11). It may indicate the synergistic effects of the rhein containing telodendrimer with DOX. The hemolytic properties of the engineered telodendrimers were evaluated in in vitro red blood cell culture to be non-observable up to 1 mg/mL concentration for 20 h incubation; while $PEG^{2k}CA_4$ and DOX-$PEG^{2k}CA_4$ showed 100% hemolysis at 37° C. after 4 hours incubation (FIG. 12—left). The MTD of the DOX-$PEG^{5k}$-$CA_4^\alpha CF_4^\epsilon$ nanotherapeutics has been determined in mice with single injection to be higher than 20 mg/Kg (FIG. 13—right). The mice treated with 25 mg/kg of DOX-$PEG^{5k}$-$CA_4^\alpha CF_4^\epsilon$ were only observed to have 17% body weight lost, which was slightly higher than the definition of MTD (15% body weight loss). The mice gain back body weight in a week after treatment. Therefore, the MTD of DOX-$PEG^{5k}$-$CA_4^\alpha CF_4^\epsilon$ should be very close to 25 mg/kg, which is 2.5 fold of those of DOX and Doxil.

Figure 14:
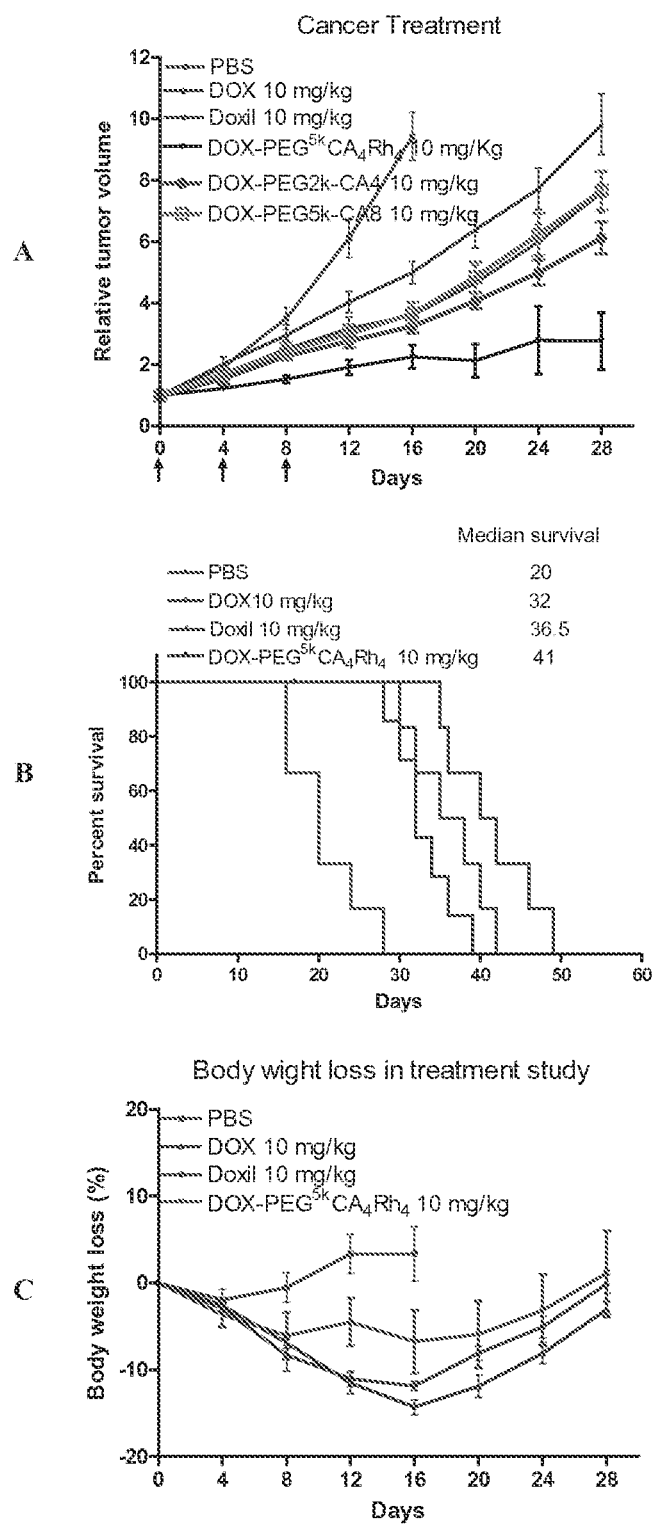
FIG. 14 shows in vivo anti-tumor efficacy (A), Kaplan-Meier survival curve (B) and body weight changes (C) after intravenous treatment of different DOX formulations in the subcutaneous Raji tumor xenograft mouse model. Tumor bearing mice (n=5-8) were administered intravenously with PBS, DOX, Doxil®, DOX-PEG$^{5k}$-CA$_4^\alpha$Rh$_4^\varepsilon$ micelles at a dose of 10 mg/kg on days 0, 4 and 8, respectively.

The nanotherapeutics have been observed to be able to target Raji cell xenograft tumor efficiently via EPR effect. Also, Raji cells have similar IC50 values for different formulations of DOX. Therefore it is reasonable to use a Raji lymphoma xenograft model to compare the in vivo anticancer efficacy of DOX nanoformulations with the clinical formulations of DOX. Free DOX, Doxil®, and DOX-$PEG^{5k}$-$CA_4^\alpha CF_4^\epsilon$ micelles at the equivalent DOX dose of 10 mg/kg (MTD of free DOX), as well as a PBS control, were administered intravenously into Raji lymphoma-bearing mice every four days on days 0, 4, and 8, respectively (n=5-8). The tumor growth inhibition and survival rate of mice in different groups were compared and the results are shown in FIG. 14—top. Compared with the control group, mice in all the DOX treatment groups showed significant inhibition of tumor growth (P<0.05). However, the tumor growth rates of mice treated with both liposomal and micellar DOX formulation were significantly lower (P<0.05), compared to those in the free DOX treatment group. It can be attributed to the higher amount of DOX that reached the tumor site via the EPR effects for both liposomal and micellar NPs. More importantly, DOX-$PEG^{5k}$-$CA_4^\alpha CF_4^\epsilon$ micelles exhibited even better tumor growth inhibition (P<0.05) than Doxil®. For example, by day 28, the median RTV was 9.9 for mice treated with free DOX, while the RTVs for mice treated with Doxil® and DOX-$PEG^{5k}$-$CA_4^\alpha CF_4^\epsilon$ micelles were 7.6 and 2.8, respectively. Compared to Doxil®, the superior tumor inhibition of DOX-$PEG^{5k}$-$CA_4^\alpha CF_4^\epsilon$ micelles could be partially explained by the deeper penetration capability throughout the tumor tissue due to their significantly smaller particle sizes (18 nm VS 140 nm) when reaching the tumor site via efficient EPR effect. Compared to DOX-$PEG^{5k}$-$CA_8$ and DOX-$PEG^{2k}$-$CA_4$ micelles, DOX-$PEG^{5k}$-$CA_4^\alpha CF_4^\epsilon$ micelles show significant enhancement in in vivo cancer treatment, which may due to its superior stability. For humane reasons, animals were euthanized when the implanted tumor volume reached 2000 $mm^3$, which was considered as the end point of survival data. The mice survival rate in each group is presented by the Kaplan-Meier survival curve, respectively (FIG. 14—middle). In general, compared to PBS control, all the DOX formulations significantly prolonged the survival rates of tumor bearing mice. However, mice treated with DOX-$PEG^{5k}$-$CA_4^\alpha CF_4^\epsilon$ micelles achieved the longest survival time among all the DOX formulations. The median survival time of mice in the group of PBS control, free DOX, Doxil®, and DOX-$PEG^{5k}$-$CA_4^\alpha CF_4^\epsilon$ micelles was 20, 32, 36.5 and 41 days, respectively.

Figure 15:
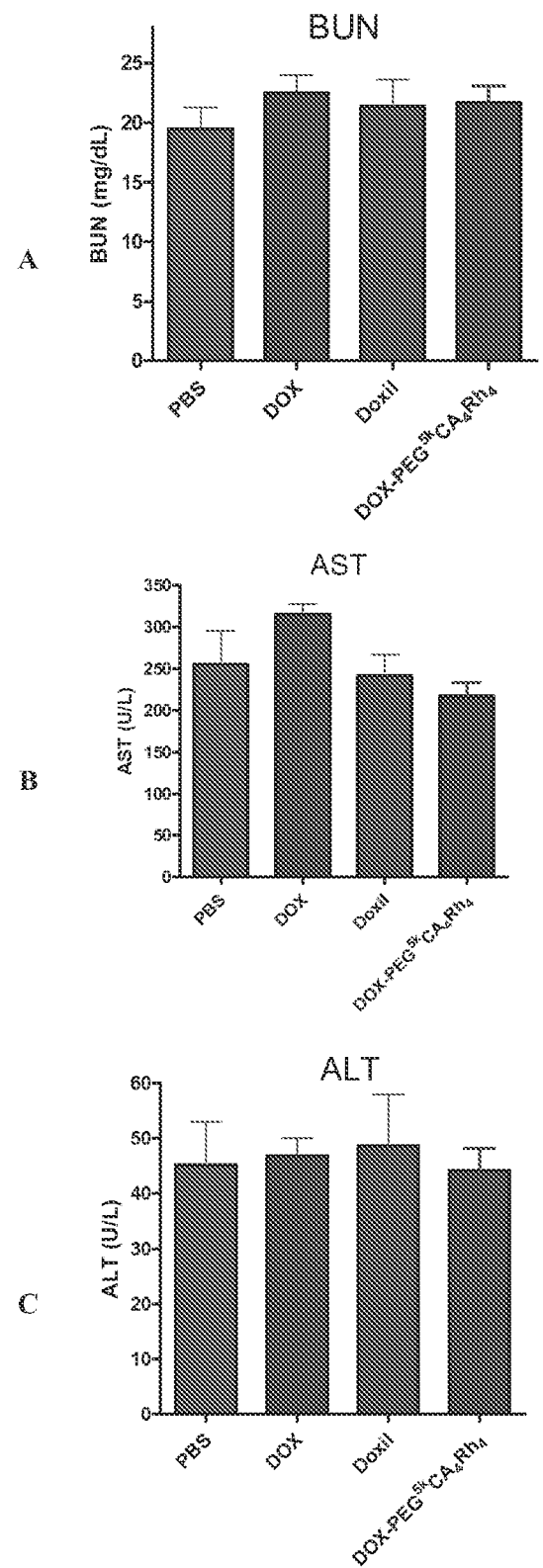
FIG. 15 shows the serum chemistry (hepatic and renal function test) in the therapeutic study, including BUN (A), AST (B) and ALT (C).
Figure 17:
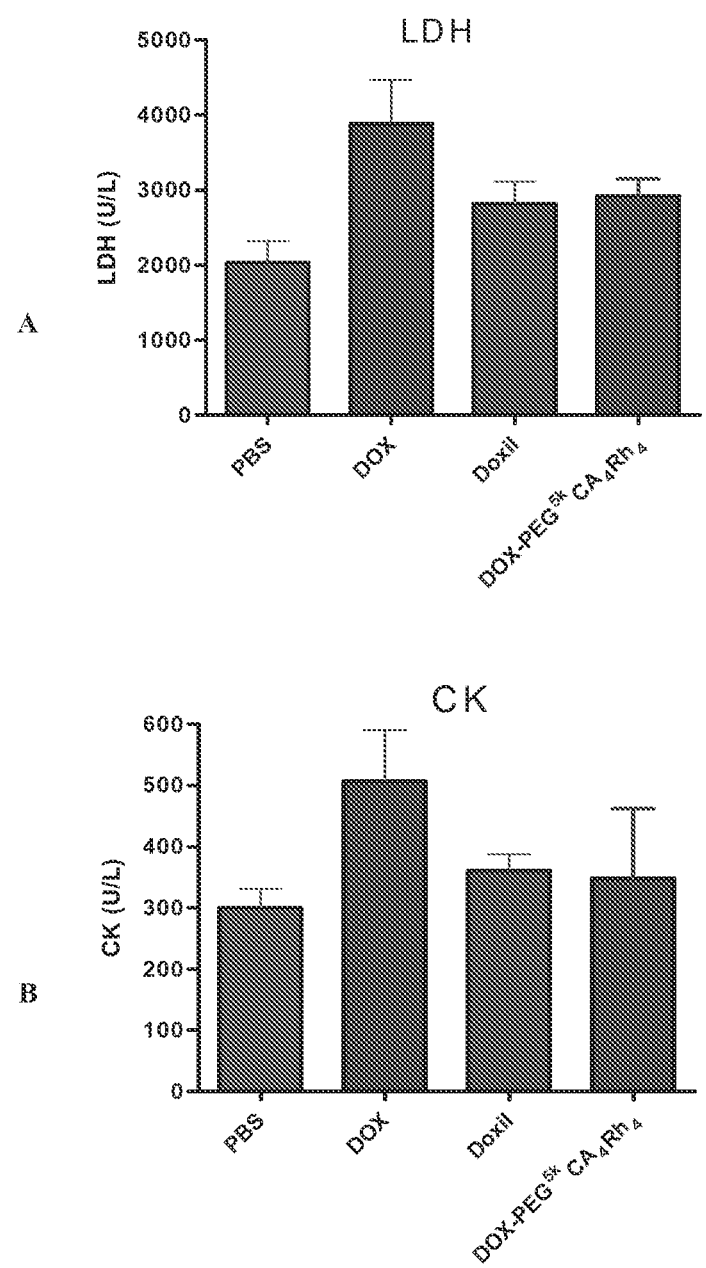
FIG. 17 shows serum levels of creatine kinase (CK, B) and lactate dehydrogenase (LDH, A) on day 7 after the last dosage of different DOX formulations in Raji tumor bearing mice. Each data point is represented as mean±SEM. *P<0.05.

The possible toxicities of all the treated mice were monitored by the body weight change, blood cell counts, and serum chemistry including hepatic and renal function panels as well as cardiac enzymes. FIG. 14—bottom presents the body weight changes of the mice in different treatment groups over time as an indication of overall systemic toxicity of different formulations. Compared to PBS control group, mice given all the DOX formulations exhibited initial body weight loss to varying extent, followed by the recovery of body weight one week after the end of treatment. However, the body weight loss of mice in the free DOX group was significantly higher than other DOX nanoformulation groups (P<0.05), leading to one death on day 16. On day 7 after the last injection, blood samples were collected for blood cell counts and serum chemistry analysis. Compared to PBS control group, the WBC count in free DOX group significantly decreased (P<0.05), whereas the WBC counts in all the DOX nanoformulations groups were within the normal range (FIG. 16). The hepatic and renal function tests including ALT, AST and BUN were within the normal ranges for all the groups (FIG. 15). Importantly, encapsulation of DOX in the DOX-PEG$^{5k}$-CA$_4^\alpha$CF$_4^\varepsilon$ micellar NPs was found to decrease the cardiotoxicity compared with free drug. Serum CK and LDH levels are two well-characterized markers for cellular damage in a variety of cardiac disease models. The induced serum level of CK and LDH enzymes in mice treated with free DOX was significantly increased (P<0.05), compared with untreated mice (FIG. 17). However, the serum CK and LDH levels were significantly lower when DOX was loaded in DOX-PEG$^{5k}$-CA$_4^\alpha$CF$_4^\varepsilon$ micelles or in Doxil, as compared to free DOX (P<0.05). The decreased cardiotoxicity of DOX micellar formulations can be attributed to the reduced uptake in the heart, as demonstrated previously in an in vivo biodistribution study. Although there were no significant findings in the histological examination of the heart at one week after completion of treatment, it is likely that the short follow-up time was not sufficient to discern major histological changes.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound selected from the group consisting of:

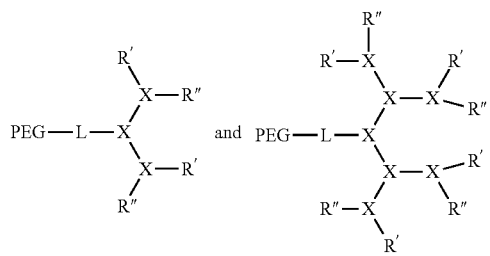

wherein
each branched monomer unit X is lysine;
L is a bond;
PEG is a polyethyleneglycol (PEG) polymer, having a molecular weight of 1-100 kDa;
R' is selected from the group consisting of cholic acid (CA), (3α, 5β, 7α, 12α)-7,12-dihydroxy-3-(2,3-dihydroxy-1-propoxy)-cholic acid (CA-4OH), (3α, 5β, 7α, 12α)-7-hydroxy-3,12-di(2,3-dihydroxy-1-propoxy)-cholic acid (CA-5OH), (3α, 5β, 7α, 12α)-7,12-dihydroxy-3-(3-amino-2-hydroxy-1-propoxy)-cholic acid (CA-3OH—NH$_2$); and
R" is selected from the group consisting of cholesterol formate (CF), doxorubicin (DOX), and rhein (Rh).

2. The compound of claim 1, wherein the compound has the formula:

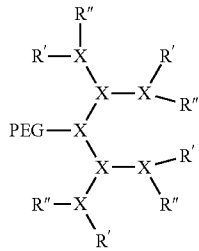

wherein
each X is lysine;
PEG is PEG5k; and
each R' is CA-4OH, or
each R' is CA-5OH, or
each R' is CA-3OH—NH$_2$.

3. The compound of claim 1, wherein the compound has the formula:

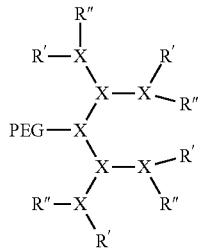

wherein
each X is lysine having an α amino and an ε amino, wherein each R' is linked to the α amino and each R" is linked to the ε amino;
PEG is PEG5k; and
each R' is CA, and each R" is CF, or
each R' is CA, and each R" is Rh.

4. A nanocarrier having an interior and an exterior, the nanocarrier comprising a plurality of compounds of claim 1, wherein each compound self-assembles in an aqueous solvent to form the nanocarrier such that a hydrophobic pocket is formed in the interior of the nanocarrier, and wherein the PEG of each compound self-assembles on the exterior of the nanocarrier.

5. A method of treating a disease, comprising administering to a subject in need of such treatment, a therapeutically effective amount of a nanocarrier of claim 4, wherein the nanocarrier further comprises a drug.

6. A method of imaging, comprising administering to a subject to be imaged, an effective amount of a nanocarrier of claim 4, wherein the nanocarrier further comprises an imaging agent.

* * * * *